United States Patent [19]
Johnson et al.

[11] Patent Number: 6,034,066
[45] Date of Patent: Mar. 7, 2000

[54] CYSTEINE PROTEASE INHIBITORS FOR USE IN TREATMENT OF IGE MEDIATED ALLERGIC DISEASES

[75] Inventors: Tony Johnson, Ely; Terrance Hart; Peter Laing, both of Cambridge; Farouk Shakib, Nottingham; Martin Quibell, Cambridge, all of United Kingdom

[73] Assignee: Peptide Therapeutics Limited, Cambridge, United Kingdom

[21] Appl. No.: 09/000,045

[22] PCT Filed: Jul. 17, 1996

[86] PCT No.: PCT/GB96/01707

§ 371 Date: Feb. 26, 1998

§ 102(e) Date: Feb. 26, 1998

[87] PCT Pub. No.: WO97/04004

PCT Pub. Date: Feb. 6, 1997

[30] Foreign Application Priority Data

Jul. 17, 1995 [GB] United Kingdom .................... 9514616
Oct. 31, 1995 [GB] United Kingdom .................... 9522221

[51] Int. Cl.$^7$ .......................... A61K 38/00; A61K 38/02; C07K 5/00; C07K 7/00
[52] U.S. Cl. .................. 514/18; 514/2; 514/19; 530/331
[58] Field of Search ...................... 530/331; 514/18–19, 514/2

[56] References Cited

U.S. PATENT DOCUMENTS 5,714,484   2/1998   Zimmermann et al. .............. 514/231.5

FOREIGN PATENT DOCUMENTS

| 26 02 750 A1 | 8/1976 | Germany . |
| 2602750 | 8/1976 | Germany . |
| 95 15748 | 6/1995 | WIPO . |
| 95/15749 | 6/1995 | WIPO . |

OTHER PUBLICATIONS

Chemical Abstracts, vol. 115, p. 764 (1991).
Chemical Abstracts, vol. 111, No. 19, p. 172077 (1989).
Chemical Abstracts, vol. 120, p. 77622 (1994).
Chemical Abstracts, vol. 118, p. 148071 (1993).
Reetz et al, "Stereoselective Nucleophilic Addition Reactions . . . ," Agnew, Chem. Int. Ed. Engl., vol. 31, No. 12, pp. 1626–1629 (1992).
Barton et al, "Synthesis of Novel α–Amino–Acids and Derivatives . . . ," Tetrahedron, vol. 43, No. 19, pp. 4297–4308 (1987).
Chemical Abstracts, vol. 124, No. 1, p. 6957 (1996).
Chemical Abstracts, vol. 123, p. 984 (1995).
Synthesis, pp. 676–678 (1983) (XP 000573896).
Chemical Abstracts, vol. 106, p. 676 (1986).
Abstract, JP 6192085 A.
Abstract, JP 7242600 A.
Synthesas, pp. 278–280 (1975).

Chemical Abstracts, vol. 115, No. 25, Dec. 23, 1991 Columbus, Ohio, US; abstract No. 277395v, G A Stewart et al.: "Fecally derived hydrolytic enzymes from Dermatophagoides pteronyssinus; physico–chemical characterization of potential allergens" p. 764 XP002018304 see abstract & Int. Arch. Allergy Appl. Immunol., vol. 95, No. 2–3, 1991, pp. 248–256.
Chemical Abstracts, vol. 111, No. 19, Nov. 6, 1989, Columbus, Ohio, US; abstract No. 172076f, Y Ino et al.: "Characterization of proteases in the crude mite extract" p. 537; XP002018305 see abstract & Int. Arch. Allergy Appl. Immunol., vol. 89, No. 4, 1989, pp. 321–326.
Chemical Abstracts, vol. 120, No. 7, Feb. 14, 1994 Columbus, Ohio US; abstract No. 77643r T Tanami et al.: "Preparation of tripeptides as cysteine protease inhinbitors" p. 923; XP002018306 see abstract & JP 05 213 990 A (Taisho Pharma Co.) Nov. 22, 1993.
Chemical Abstracts, vol. 118, No. 15, Apr. 12, 1993 Columbus, Ohio, US; abstract No. 148069e T Tanami et al.: "Preparations of tripeptide aldehyde derivatives as cysteine protease inhibitors" p. 891; XP002018307 see abstract & JP 04 273 896 A (Taisho Pharma Co.) Sep. 30, 1992.
Angelwandte Chemie International Edition., vol. 31, No. 12, Dec. 1992, Weinheim DE, pp. 1626–1629, XP002018302 M T Reetz et al.: "Stereoselective nucleophilic addition reactions of reactive pseudopeptides" see whole document.
Tetrahedron vol. 43, No. 19, 1987, Oxford GB pp. 4279–4308, XP002018303 D H R Barton et al.: "Synthesis of novel alpha–amino acids and derivatives using radical chemistry; synthesis of L–and D–alpha–amino adipic acids, L–alpha–aminopimelic acid andappropriate unsaturated derivatives" see whole document.
Chemical Abstract, vol. 124, No. 1, Jan. 1, 1996 Columbus, Ohio, US; abstract No. 6947q O Schulz et al.: Der p I, a major allergen of the dust mite, proteolitically cleaves the low–affinity receptor for human IgE (CD23) p. 755; XP002018309 see abstract & Eur. J. Immuno., vol. 25, No. 11, 1995, pp. 3191–3194.

(List continued on next page.)

*Primary Examiner*—Avis M. Davenport
*Attorney, Agent, or Firm*—Nixon & Vanderhye

[57] ABSTRACT

The invention provides compounds for use in the treatment of allergic diseases including juvenile asthma and eczema. The compounds can inhibit IgE mediated reaction to major environmental and occupational allergens and can also have a prophylactic effect against allergic disease by preventing allergic sensitization to environmental and occupational allergens when administered to at-risk individuals (e.g., those at genetic risk of asthma and those exposed to occupational allergens in the workplace). The compounds are also useful for inactivation or attenuation of the allergenicity of allergens in situ. The invention provides compounds and ligands per se, pharmaceutical compositions containing the compounds, processes for producing the compounds and pharmaceutical compositions, and methods for using the compounds and compositions in treatment or prophylaxis of IgE mediated allergic diseases and in inactivation or attenuation of allergens in situ. The invention also enables the reduction or destruction of the viability of allergy-causing organisms.

14 Claims, 12 Drawing Sheets

OTHER PUBLICATIONS

Chemical Abstracts, vol. 123, No. 21, Nov. 20, 1995 Columbus, Ohio, US; abstract No. 283510L, C R A Hewitt et al.:"A major house dust kite allergen disrupts the immunoglobulin E network by selectively cleaving CD23; innate protection by antiprotease" p. 984; XP002018310 see abstract & J. Exp. Med., vol. 182, No. 5, Nov. 1995, pp. 1537–1544.

Synthesis No. 8, Aug. 1983, Stuttgart DE, pp. 676–678, XP000573896 J–A_Fehrentz & B Castro: "An efficient synthesis of optically active alpha–(t–butoxycarbonylamino)–aldehydes from alpha–amino acids" see whole document.

Synthesis, No. 4, Apr. 1975, Stuttgart DE, pp. 278–280, XP002019662 M Mikolajczyk et al.; "Synthesis of alpha-–beta–unsaturated sulphides, sulphoxides, and sulphones by the Horner–Wittig reaction in two–phase system catalysed by quaternary ammonium salts and crown ethers" see p. 279.

Chemical Abstracts, vol. 105, No. 3, Jul. 21, 1986 Columbus, Ohio, US; abstract No. 24605p J–A Fehrenz et al.: "Synthesis of aldehydic peptides inhibiting renin" p. 676 XP002019663 see abstract & International Juornal of Peptide and Protein Research, vol. 26, No. 3, Mar. 1985, pp. 236–241.

Compound 8

Compound 40

Compound 25

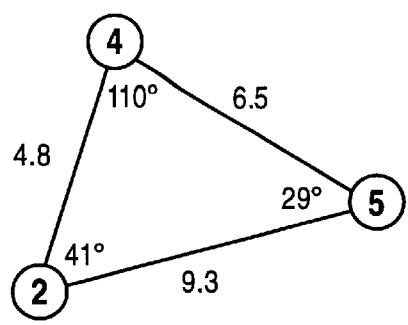
Fig. 15
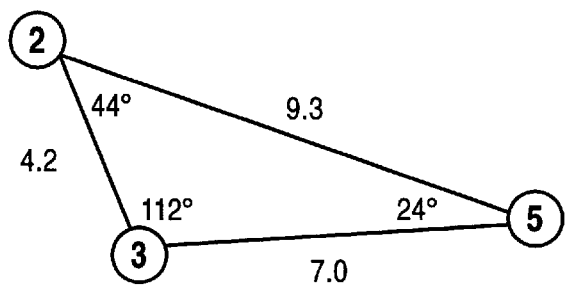
Fig. 14
Fig. 17
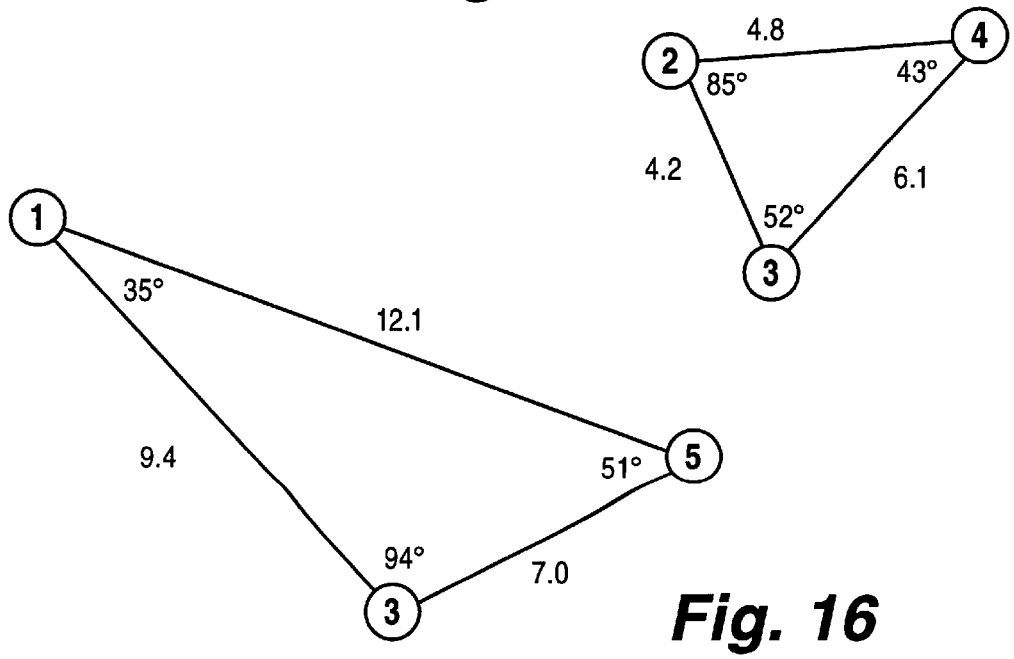
Fig. 16

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

```
Thr Asn Ala Cys Ser Ile Asn Gly Asn Ala
1               5                   10
```

CYSTEINE PROTEASE INHIBITORS FOR USE IN TREATMENT OF IGE MEDIATED ALLERGIC DISEASES

FIELD OF THE INVENTION

The invention relates to compounds for use in the treatment of allergic diseases including juvenile asthma and eczema.

Compounds of the invention can inhibit IgE mediated reaction to major environmental and occupational allergens. They can also have a prophylactic effect against allergic disease by preventing allergic sensitisation to environmental and occupational antigens when administered to at-risk individuals (e.g. those at genetic risk of asthma, and those exposed to occupational allergens in the workplace). The compounds of the invention can also be useful for inactivation or attenuation of the allergenicity of allergens in situ. The invention provides novel compounds and ligands per se, pharmaceutical compositions containing the compounds, processes for producing the compounds and pharmaceutical compositions, and methods for using the compounds and compositions in treatment or prophylaxis of IgE mediated allergic diseases and in inactivation or attenuation of allergens in situ. The invention also provides means for the reducing or destroying the viability of allergy-causing organisms.

The invention is made possible by our new understanding of the role of the low-affinity receptor for IgE (FceRII), also known as CD23, in IgE mediated allergic diseases.

DESCRIPTION OF THE RELATED ART

The Multiple Roles of CD23 CD23 plays an important role in the regulation of immune responses—particularly the regulation of IgE responses. CD23 is a cell surface protein which extends from the plasma membrane via a stalk which is cleaved proteolytically during immune responses. We have demonstrated that CD 23 is cleaved by Der p I; a protease which is the major allergen of the house dust mite, although the endogenous proteases responsible or cleaving CD 23 have not so far been identified. In its membrane bound form, CD23 acts as a cellular receptor for IgE and is found on various cell types including B cells, T cells, platelets, eosinophils, keratinocytes and also on antigen presenting cells (including follicular dendritic cells) which present antigens to T and B lymphocytes. The level of expression of CD23 at the cell surface determines its functionality and is regulated by cytokines, notably IL4.

In its membrane bound form, CD23 allows eosinophils to attach to parasites via antigen-specific IgE. It also plays an important regulatory role on B lymphocytes (which produce antibodies). In the presence of soluble IgE, probably in the form so immune complexes with the allergen, cell surface CD23 becomes occupied by IgE, conveying an inhibitory signal to the B-lymphocyte. This is believed to be an important negative feedback loop in the regulation of IgE synthesis. Occupancy of membrane bound CD23 by IgE protects CD23 from proteolytic cleavage, preventing the release of "cytokine active" forms of soluble CD23 (see below) which favour the production of IgE as opposed to other classes of immunoglobulin. CD23 also interacts with ligands (or "counterstructures") other than IgE. By association of CD23 on an activated B cell with CD21 (the type two complement receptor "CR2") on a follicular dendritic cell of the lymph node, cell-surface CD23 functions as an intercellular adhesion molecule. This function of CD23 is believed to be important in the rescue of germinal centre B lymphocytes from "apoptosis" (i.e. programmed cell-death), allowing the survival of antibody producing clones which would otherwise have been destined to die. There is also evidence that CD23 associates with the cell-surface molecules responsible for presenting antigenic peptides to T lymphocytes (i.e. the HLA class-II molecules) and may thereby influence antigen presentation to T lymphocytes. Moreover, the presence and degree of expression of CD23 on Langerhans cells (a type of antigen presenting cell), and its affinity for immune complexes comprised of allergen and IgE, will also determine to what extent such complexes are processed and presented to T lymphocytes. CD23 may therefore influence antigen presentation to both B and T lymphocytes, processes which determine the degree and nature of immune responsiveness to foreign antigens.

Proteolytic cleavage of CD23 Native CD23 (45 ka) can be cleaved from the cell surface by proteolytic digestion at several sites within the stalk region to generate soluble CD23 (sCD23). The largest soluble fragment is of 37 kDa. Cleavage nearer the membrane-distal lectin domain gives soluble fragments of 33, 29 and 25 kDa containing the lectin domain and a C-terminal tail. Some forms of sCD23 (notably the 37 kDa form) are active upon ocher cells. Thus, Ghadieri et al and Bonnefoy et al have demonstrated that sCD23 (37 kDa) is a potent stimulator of mast cells—eliciting degranulation at nanograms per ml concentrations. Moreover, the larger forms of sCD23 also have cytokine activities which favour the production of IgE and IgG4 subclass antibodies associated with allergic, anti-parasitic and chronic immune responses. Indeed in vitro experiments have shown that in the presence of IL4 sCD23 induces IgE producing B cells to differentiate into plasma cells (Liu; Gordon). The regulatory role of CD23 upon IgE synthesis has also been confirmed in vivo using antibodies to CD23 (which inhibit antigen-specific IgE responses), and using CD23 gene-knockout mice, in which antigen-specific IgE responses are exaggerated.

In addition to these data from experiments in animals elevated levels of sCD23 and of CD23 positive peripheral blood lymphocytes have been reported in atopic individuals (Gordon et al) (Ghadieri et al) implicating CD23 as an important regulatory factor in IgE immune responses.

From these considerations it its evident that CD23 has important regulatory functions determining the quality and quantity of an immune response, particularly affecting humoral immunity (i.e. the production of specific antibodies). Moreover, the physical form of CD23 (i.e. cellular versus soluble) has a major influence on its regulatory function, particularly in the case of the IgE responses of B lymphocytes. Thus, CD23 in its cellular form participates in the negative feedback inhibition of IgE synthesis. By contrast, in its soluble forms CD23 stimulates the production of IgE via its cytokine activities. The balance between cellular and soluble forms of CD23 is therefore seen to have a pivotal role in determining the character of an immune response, in particular whether IgE is produced against a particular antigen, and also how much IgE is produced. However, the nature of proteases which bring about the cleavage of CD23 and which determine the balance between membrane bound and soluble forms has not so-far been established, although current theory, supported only by circumstantial evidence, has it that CD23 is autocatalytic, and brings about its own cleavage from the plasma membrane.

Proteolytic activity of certain environmental and occupational allergens. Studies in mice and in man suggest that allergic sensitising potency of environmental allergens is, in some cases, related to their proteolytic activity. Thus, papain (a cysteinyl protease of papaya) is a potent allergen in man. Also, inhaled bromelain (a cysteinyl protease of pineapple) causes occupational allergies and asthma (Gailhoffer 1988). Also, the major allergen of house dust mite (Der p I), to which many asthmatic individuals are sensitive, has proteolytic activity. Proteolytic enzymes of environmental antigens and parasites may influence the quality of T lymphocyte responses to favour IgE production (reviewed by Finkelmann 1992) although how they do so has not been established. Thus, subcutaneous daily injections of certain strains of mice with papain result in a dramatic increase in non-specific IgE which is markedly attenuated by prior inactivation of the catalytic activity of the enzyme. The elevation of total IgE by active papain is associated with the production of cytokines characteristic of the $T_k2$ subset of T-helper lymphocytes which are involved in allergic and anti-parasitic responses. However, the substrate of this proteolytic mechanism whereby papain elevates IgE production has not been identified.

SUMMARY OF THE INVENTION

Current teaching has it that CD23 is cleaved from the plasma membrane by a putative autoproteolytic activity (i.e. a proteolytic activity of CD23 itself upon CD23 as a substrate). No candidate protease (either endogenous or exogenous) other than CD23 has been proposed. Moreover, the putative "autoproteolytic" activity of CD23 has never been demonstrated. Surprisingly therefore, it has now been found that the exogenous protease and allergen Der p I, in highly purified form, is very effective and specific at cleaving CD23 from the plasma membrane of cultured B lymphocytes. Since the cleavage of CD23 is an important regulatory step governing IgE synthesis, it follows that the potent allergic sensitising activity of Der p I (i.e. its allergenicity) resides, in part, in its ability to cleave CD23 from the cell surface. Although it had been speculated previously that the proteolytic activity of Der p I might be related to its allergenicity, no explanation had been offered for the mechanism of the putative proteolytic event, nor has any candidate previously been proposed as a substrate of this proteolytic activity.

In a first aspect of the invention, we have demonstrated that the cleavage of CD23 by (Gordon et al) is: i) stimulated by cysteine; ii) inhibited by the specific cysteinyl protease inhibitor E64; and iii) not inhibited by the trypsin protease inhibitor alpha-1-antitrypsin (which inhibits various trypsin-like proteases as well as trypsin). The compound E64 is L-trans-epoxysuccinyl-leucylamido (4-guanidino) butane (Sigma, Poole, UK).

These findings demonstrate that Der p I is indeed a cysteinyl protease as suggested tentitively by earlier studies, and moreover that it is the cysteinyl protease activity of Der p I which is responsible for CD23 cleavage.

From these considerations, it follows that compounds of this invention other than E64, yet capable (like E64) of inhibiting cysteinyl proteases, would also prevent the cleavage of CD23 by Der p I. This would include the peptide sequence comprising the cleavage sites of CD23 which are cleaved by Der p I, and analogues thereof. The latter would include D-amino acid analogues, including "reverse-D" peptides made exclusively of D-amino acids but of the reverse sequence of the natural cleavage site—as described recently by Van Regenmortal et al for biologically active analogues of CD4.

In a second aspect of the invention, we have now also demonstrated that the protease inhibitor human alpha-1-antitrypsin, rather than inhibiting Der p I, is a substrate for Der p I becoming cleaved at a specific site. Since Jul. 17, 1995, this site has been identified as "QVS/SGF" (Kalsheker N. et al 1996). It follows that peptide analogues (as described above for CD23 cleavage sites) and non-peptide mimetics of this site may also be specific inhibitors of Der p I. Such compounds of this invention may therefore have uses as described above for inhibitors of Der p I (i.e. prevention of in vivo cleavage of CD23 by Der p I). Moreover, since Der p I is an extracorporeal digestive enzyme of the house dust mite, it follows that inhibitors of Der p I may cause the dust mite to have "indigestion" (i.e. nutritional deprivation) due to the failure of this enzyme. Indeed, since the food of the house dust mites is comprised mainly of human skin flakes (which contain alpha-1-antitrypsin) it may be necessary to Der p I to destroy or inactivate alpha-1-antitrypsin in order to digest the skin flakes. Thus, in a third aspect of the invention inhibitors of Der p I are predicted to have a "toxic" effect (via nutritional deprivation) on house dust mites.

Inhibitors of Der p I may be useful for killing house dust mites in situ, in addition to attenuating the allergenicity (i.e. sensitising activity) of Der p I. We believe that these effects would synergise resulting in a highly effective anti-asthma agent for application to furnishings (beds, carpets etc.) which are the natural habitat for house dust mites.

We have demonstrated that the principal cleavage fragment of the native 45 kDa form of CD23 released by Der p I is indistinguishable (by SDS electrophoresis) from the major naturally occurring cleavage fragment of CD23: i.e. the 25 kDa fragment. However, sequence analysis of the N-terminal of the fragment liberated by Der p I demonstrates that the cleavage site "QVS/SGF" recognised by Der p I is distinct from the natural cleavage site that generates the 25 kda fragment. Smaller amounts of larger (presumably "cytokine active") forms of CD23 were also generated by Der p I, indicating the existence of additional, more membrane proximal cleavage sites in the stalk region. A further cleavage site has also been identified by us in the C terminal tail region as SAE/SMG.

Since inhibitors of the CD23 cleavage activity of Der p I (such as E64 and analogues) may also inhibit the endogenous protease(s) that cleave CD23, whether or not these proteases are identical in specificity to Der p I the invention therefore includes inhibitors of endogenous proteases that cleave CD23 in addition to exogenous proteases such as Der p I and bromelain and certain other environmental allergens with proteolytic activity. Where legally permissible, the invention includes the use of inhibitors of the enzymatic cleavage of CD23 (whether by endogenous or exogenous proteases) for the treatment of allergic diseases such as juvenile asthma and eczema, and the use of such inhibitors to inactivate the proteolytic activities of environmental sensitising agents or allergens such as Der p I and bromelain.

In a third aspect the invention provides novel compounds which have cysteinyl protease inhibitor activity and are capable of inhibiting proteolytic cleavage of membrane bound CD23 in vivo excluding L-trans-epoxysuccinyl-leucylamido (4-guanidino) butane (E64).

In a forth aspect the invention provides cysteinyl protease inhibitor compounds which include a chemical composition capable of adopting a structure essentially equivalent to an inhibitor of the enzyme Der p I, excluding E64, optionally together with a pharmaceutically acceptable carrier or excipient for use in the treatment of allergic diseases.

In a fifth aspect the invention provides cysteinyl protease inhibitor compounds capable of adopting a structure having a pharmacophoric pattern essentially equivalent to the pharmacophoric pattern of a section of an inhibitor of Der p I, excluding E64.

In a sixth aspect the invention provides a ligand which cross reacts with a cysteinyl protease inhibitor compound which inhibits the enzyme Der p I, excluding E64, which compound includes 1 or more copies of a motif which comprises:
i) a hydrogen bond donor;
ii) three hydrophobes; and
iii) a hydrogen bond acceptor.

In a seventh aspect the invention provides compounds or ligands of the general formula (I):

$$R_1-\underset{\underset{}{\overset{\overset{O}{\|}}{C}}}{}-\underset{\underset{H}{|}}{N}-X-\underset{\underset{H}{|}}{\overset{\overset{R_2}{|}}{C}}-\underset{\underset{H}{|}}{\overset{\overset{O}{\|}}{N}}-Y-\underset{\underset{H}{|}}{\overset{\overset{R_3}{|}}{C}}-\underset{\underset{H}{|}}{\overset{\overset{O}{\|}}{N}}-\underset{\underset{H}{|}}{\overset{\overset{R_4}{|}}{C}}-\underset{\underset{H}{|}}{N}-Z-W \quad (I)$$

wherein X, Y and Z are N or CH;
$R_1$ is a blocking group for the N-terminal nitrogen;
$R_2$, $R_3$, and $R_4$ are side-chains on X, Y, and Z; and
W is a group that reacts irreversibly with an active cysteine thiol of Der p I.

In a eighth aspect the invention provides an agent for treatment of IgE mediated allergic disease which includes as active ingredient an effective amount of a compound selected from the group consisting of: a cysteinyl protease inhibitor; a substrate for Der p I which reacts with Der p I at a specific site; and a Der p I inhibitor capable of inhibiting the proteolytic enzyme activity of Der D I, the agent optionally including one or more of a pharmaceutically acceptable carrier, adjuvant or excipient.

In a ninth aspect the invention provides an agent for attenuating or inactivating the allergenicity of Der p I which includes as active ingredient an effective amount of a compound having Der p I inhibitor activity, the agent optionally including one or more of a carrier, adjuvant, excipient.

In a tenth aspect the invention provides an agent for reducing or destroying the viability of house dust mites which includes as active ingredient an effective amount of a compound having Der p I inhibitor activity, the agent optionally including one or more of a pharmaceutically acceptable carrier, adjuvant, excipient.

In an eleventh aspect the invention provides a process for producing a compound or ligand of the invention which comprises synthesising a cysteinyl protease inhibitor compound or ligand and optionally conjugating said compound or ligand to a carrier Therefore, in summary, the present invention is based upon our appreciation that the major allergen of house dust mite faeces (Der p I), is capable of cleaving CD23 (the low affinity receptor for IgE) from the cell-surface of B-lymphocytes and presumably from other cell types. We demonstrate that this activity is stimulated by cysteine and can be abolished by the well-known cysteinyl protease inhibitor E64.

The invention relates particularly to compounds capable of inhibiting the proteolytic cleavage of CD23 from the plasma membrane of cells by exogenous proteases (such as Der p I) bromelain and certain proteases and parasites) and to compounds capable of inhibiting endogenous proteases which cleave CD23 from the cell.

The compounds may also have a prophylactic effect against allergic disease—by preventing allergic sensitisation to environmental and occupational antigens when administered to at-risk individuals (e.g. those at genetic risk of asthma, and those exposed to occupational allergens).

The compounds may also be used for the inactivation of the proteolytic activity of environmental allergens in situ (e.g. house dust mite faecal allergen Der p I in beds, carpets and vacuum cleaners). Inactivation of the proteolytic activity of these allergens may attenuate their allergenicity (i.e. their capability to provoke allergies and asthma) which is due to their capability to cleave CD23 from the cell-surface.

The compounds may also kill house dust mites by nutritional deprivation.

The present invention will now be described by way of non-limiting examples only, with reference to FIG. 1 to 18 in which:

FIG. 14 shows the distance and angle constraints between points 2–3–5 of the pharmacophore of FIG. 4.

FIG. 15 shows the distance and angle constraints between points 2–4–5 of the pharmacophore of FIG. 4.

FIG. 16 shows the distance and angle constraints between points 1–3–5 of the pharmacophore of FIG. 4.

FIG. 17 shows the distance and angle constraints between points 2–3–4 of the pharmacophore of FIG. 4.

EXAMPLES

Here we demonstrate that Der p I, a major allergen of house dust mite (*Dermatophagoides pteronyssinus*), cleaves CD23 from the surface of cultured human B cells (RPMI 8866 B cell line). The cleavage of the receptor from the B cell surface was associated with a parallel increase in sCD23 in the culture supernatant. Labelled antibody experiments and protease inhibition assays clearly demonstrate that Der p I is a cysteine protease that directly cleaves a 25K fragment of CD23. The proteolytic affect of Der p I has specificity for CD23, since none of the other B cell markers tested (CD20, HLA-DR, CD71 and CD49d) were affected.

These data suggest that Der p I elicits IgE antibody responses in 80% of patients suffering from dust mite allergy, by its ability to proteolytically release sCD23, and thereby upregulate IgE synthesis.

Figure 1:
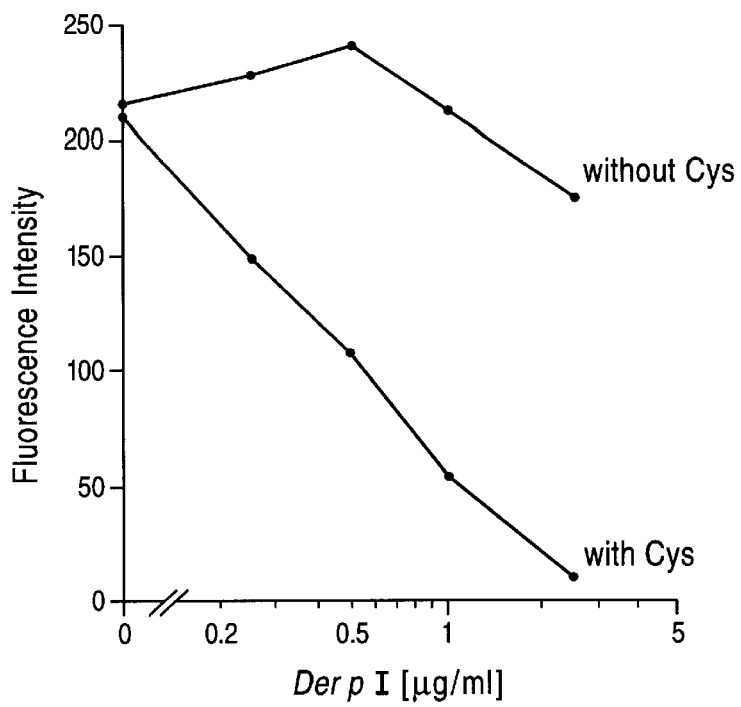
FIG. 1 shows CD23 expression by RPMI 8866 human 3 cells using FITC labelled mouse monoclonal anti-CD23 antibody.
Figure 2:
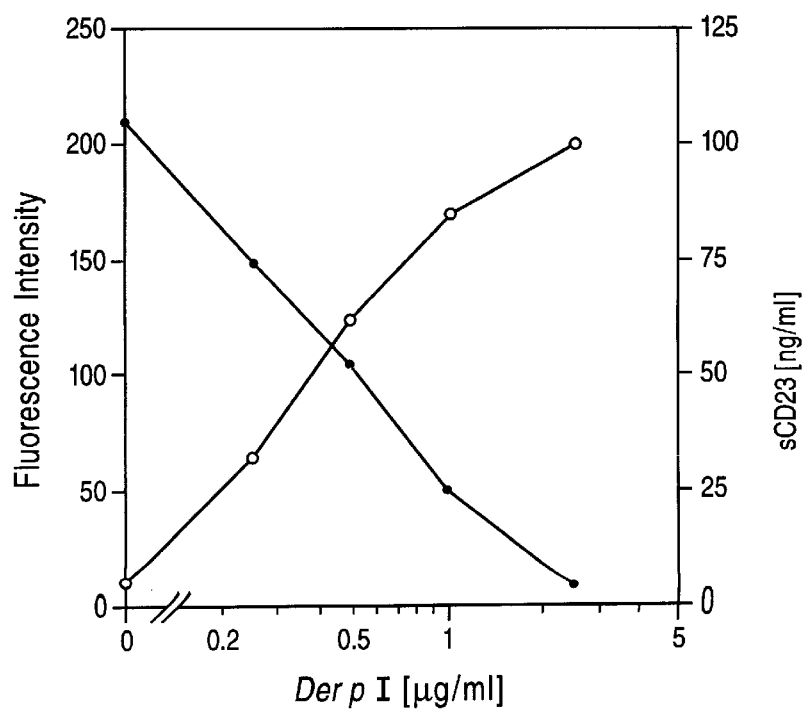
FIG. 2 shows that the proteolytic effect Der p I is specific for CD23.
Figure 3A:
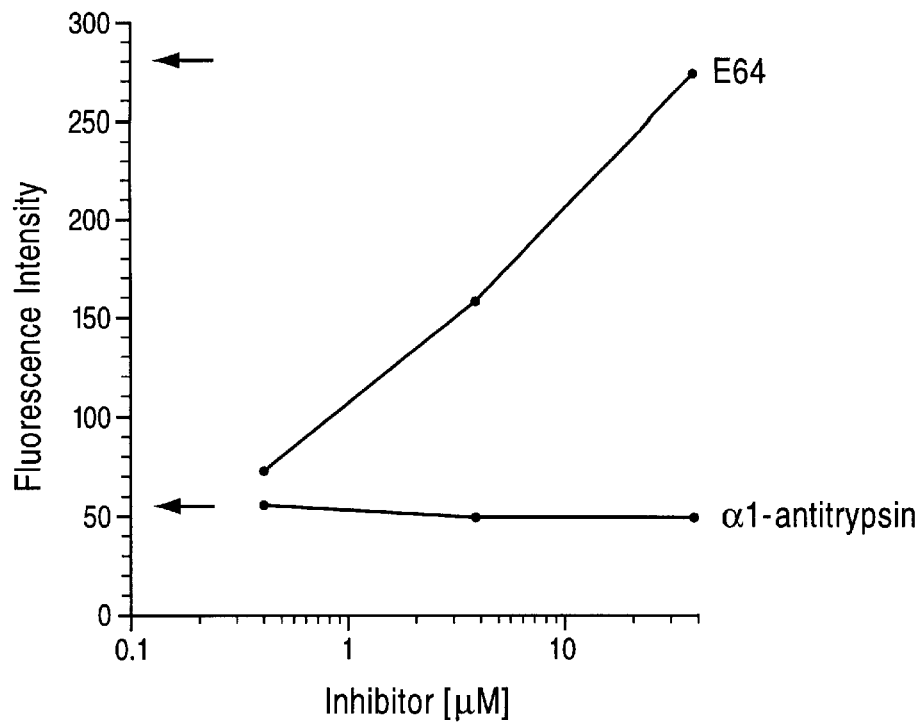
FIG. 3 shows that Der p I preferentially cleaves CD23 close to the lectin domain.
Figure 3B:
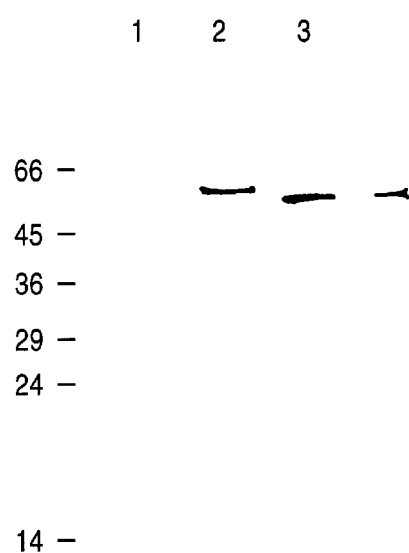
Figure 3C:
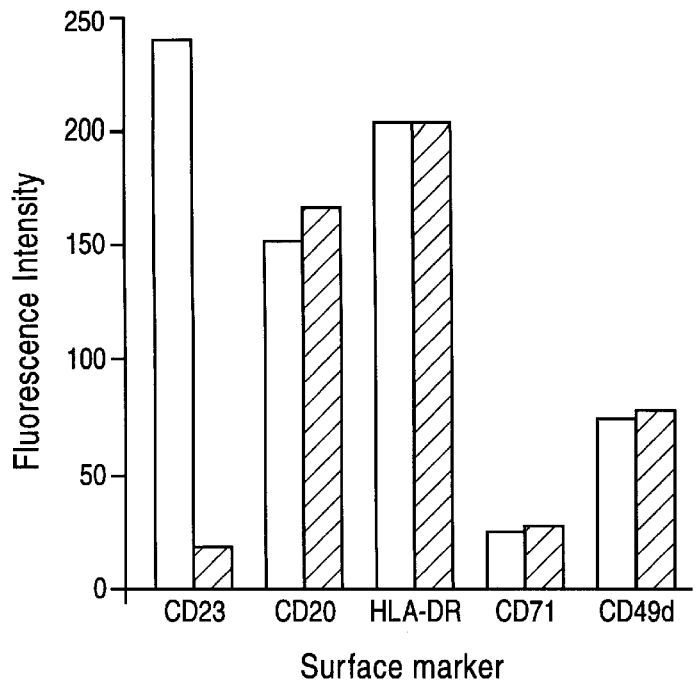
Figure 3D:
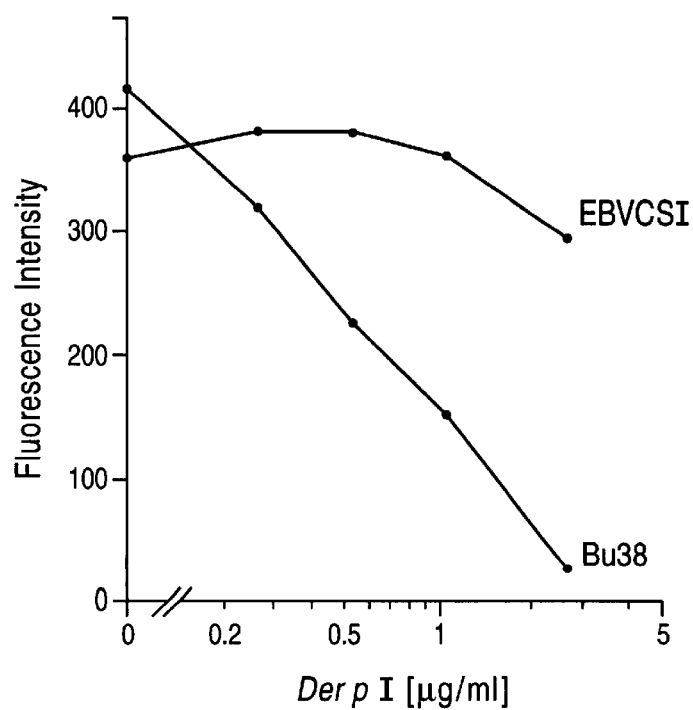

We have affinity purified Der p I from dust mite extract and tested its ability to proteolytically cleave CD23 expressed on cultured RPMI 8866 B cells, using FITC labelled monoclonal anti-human CD23 (Bu38). The data show that, in the presence of cysteine (5 mM), Der p I cleaves in a dose-dependent manner membrane CD23, thereby releasing sCD23 into the culture supernatant (FIG. 1a and 1b). The proteolytic activity of Der p I was inhibited by E64 (a cysteine protease inhibitor), but not by alpha-1-antitrypsin (a serine protease inhibitor), thereby confirming the cysteine protease nature of Der p I (FIG. 1c). We have in fact demonstrated that Der p I completely cleaves alpha-1-antitrypsin (1:10 molar ratio) to yield a degradation pattern (FIG. 1d) similar to that generated by papain, a well characterised cysteine protease. A more detailed description of FIG. 1 is as follows:

Cells were analysed on a FACScan (Becton Dickinson, Oxford, UK) with a linear fluorescence setting of 660 volts. The fluorescence (FL1) profile versus forward scatter (FSC) was used to monitor the cells, the amplification scale was altered according to the level of fluorescence. For each sample 4000 events were collected and then analysed using the flowMATE programme (DAKO, High Wycombe, UK). Data presented are representative of 3 replicate experiments, each point in a to c represents the mean of duplicate determinations, FIG. 1(a). Dose and cysteine dependency of CD23 cleavage by Der p I (for method of purification see FIG. 1(d) below). Der p I was pre-incubated (15 min at 37° C.) with or without 5 mM cysteine and added to 2–3×10$^5$ RPMI 8866 cells in a total volume of 200 ml RPMI 1640+10 mM HEPES. The mixture was then incubated (1 h at 37° C.) and the cells, collected by centrifugation, were washed in RPMI 1640+10 mM HEPES and incubated (30 min at room temperature) with FITC conjugated anti-CD23 monoclonal antibody (Bu38, The Binding Site, Birmingham, UK). FIG. 1(b). Cleavage of membrane CD23 was associated with a parallel dose dependent release of sCD23 in the culture supernatant. The supernatant was collected from cultured RPMI 8866 cells treated with Der p I (as described above) and diluted 1/5 for sCD23 determination by ELISA (open circles) (The Binding Site, Birmingham, UK). In this ELISA there was no cross-reactivity between Der p I and sCD23. FIG. 1(c). Class specific inhibitor of cysteine proteases prevent membrane CD23 cleavage by Der p I. E64 (L-trans-epoxysuccinylleucylamido (4-guanidino) butane) (Sigma, Poole, UK) completely inhibits cleavage of CD23 by Der p I, whereas no such inhibitory effect was demonstrable with alpha-1-antitrypsin, a naturally occurring human serine protease inhibitor. One hundred ml of 5 g/ml Der p I was pre-incubated (30 min at 37° C.) with 10 ml of either E64 or alpha-1-antitrypsin and then added to the RPMI 8866 cells (as described above). The arrows indicate level of CD23 expression in the absence (upper arrow) and presence (lower arrow) of Der p I. FIG. 1(d). Silver stain SDS-PAGE (12% gel) analysis of the Der p I preparation, human alpha-1-antitrypsin and the effect of Der p I on alpha-1-antitrypsin. Der p I was purified by affinity chromatography using anti-Der p I antibody (4Cl, Indoor Biotechnologies, Clwyd, UK). The purity of the preparation was confirmed by N-terminal sequencing carried out on an automatic amino acid sequencer (Applied Biosystems, Foster City, Calif., USA). The sequence obtained (Thr-Asn-Ala-Cys-Ser-Ile-Asn-Gly-Asn-Ala, or TNACSINGNA SEQ ID No. 1) matches the published sequence of Der p I. The activity of the alpha-1-antitrypsin preparation was ascertained by active site titration against bovine chymotrypsin (Dr. David Lomas, personal communication). The gel shows single bands for Der p I (lane 1) and alpha-1-antitrypsin (lane 2). Incubation (2 h at 37° C.) of Der p I (0.25 mg) with alpha-1-antitrypsin (5 mg), in a total volume of 10 ml, results in the cleavage of a large fragment (arrow) from alpha-1-antitrypsin (lane 3). This pattern is in agreement with that generated by papain. The mass standards are indicated on the left. To investigate the enzymatic specificity of Der p I for CD23, we monitored the expression of other B cell markers following treatment with 2.5 mg/ml (final concentration) of Der p I. At this Der p I concentration, which has been shown to give maximum cleavage of CD23 (FIG. 1a), there was no significant loss of CD23, HLA-DR, CD71 and CD49d expressions (FIG. 2). A more detailed description of FIG. 2 is as follows:

RPMI 8866 cells were treated with 100 ml of 5 mg/ml Der p I and the expression of membrane CD23 was monitored in parallel with other B cell surface markers (CD20, HLA-DR, CD71 and CD49d). These markers were detected using anti-CD20 (L27), anti-HLA-DR (L243) (Becton Dickinson, Oxford, UK), anti-CD71 (Ber-T9) (Dako, Buckinghamshire, UK) and anti-CD49d (HP2.1) (Immunotech, Westbrook, Me., USA) antibodies respectively. Paired results represent the expression of markers in the absence (open bars) and presence (solid bars) of Der p I. Data presented are representative of 3 replicate experiments, each point represents the mean of duplicate determinations.

To gain insight as to the Der p I cleavage site on CD23, we onitored the proteolytic cleavage process using Bu38 and EBVCSI monoclonal anti-CD23 antibodies, which are directed against the lectin domain and the stalk region respectively. Thus, Bu38 detects all fragments down to 25 kDa, whereas EBVCSI recognises only fragments larger than 25 kDa (J. Gordon, personal communication). The results show that Der p I cleaves CD23 at a site close to the lectin domain, since EBVCS1 antibody was still capable of binding to the residual membrane bound portion of the receptor (FIG. 3). However, at a Der p I concentration of greater than 1 mg/ml there also appeared to be some cleavage of CD23 fragments larger than 25 kDa. Since the highest concentration of Der p I (2.5 g/ml) resulted in complete loss of Bu38 binding and only partial loss of EBVCS1 binding, the preferred site of initial cleavage of CD23 by Der p I appears to be close to the lectin domain. A more detailed description of FIG. 3 is as follows:

RPMI 8866 cells were treated with Der p I, as described above, and the expression of membrane CD23 was monitored using two monoclonal anti-CD23 antibodies: Bu38 (recognises the lectin domain) and EBVCS1 (recognises the stalk region between 25 kDa fragments). Thus, Bu38 recognises the intact molecule and all soluble fragments, while EBVCS1 recognises the intact molecule and the residual membrane bound portion after cleavage of the 25 kDa fragment (sCD23) (J. Gordon, personal communication). The experiment demonstrates that Der p I, at concentrations of up to 1 mg/ml, preferentially releases a 25 kDa fragment of CD23. Data presented are representatuve of 3 replicate experiments, each point represents the mean of duplicate determinations.

The preferred cleavage site of CD23 giving rise to the 25 kD fragment has been identified by us as detailed above.

Soluble CD23 is one of the signals known to induce IgE producing B cells to become plasma cells which are required for IgE production. Therefore the nature of the proteases that cleave CD23 in vivo is of considerable interest. Although it has been suggested that CD23 has autoproteolytic activity, we were previously unaware of what proteases cleave membrane CD23. We have demonstrated that Der p I, an exogenous cysteine protease, fulfils this function. Der p I elicits IgE antibody responses in 80% of patients suffering from dust mite allergy, and there is in vivo evidence that such patients have high circulating levels of sCD23. This ubiquitous inhaled allergen is clearly highly immunogenic, and we believe its immunogenicity may be due in part to its enzymatic activity. It has indeed been demonstrated that the allergenicity of papain, a cysteine protease showing sequence homology with Der pI, is highly related to its enzymatic activity.

The demonstration that Der p I proteolytically cleaves membrane CD23 raises the question of the role of IgE in the allergic process. Firstly, IgE specific to Der p I could target Der p I to B lymphocytes and other CD23 bearing cells (e.g. eosinophils), thereby helping to build a high concentration of this allergen on the cell surface. Secondly, the binding of IgE to CD23 may protect the receptor from proteolytic attack by Der p I.

Purification of Der p I Protein

Crude mite extract (~100 mg, SmithKline-Beecham) was dissolved in 5 ml Phosphate Buffered Saline (PBS; 50 mM potassium phosphate; pH 7.4 containing 150 mM NaCl). Der p I was purified by affinity column chromatography using 4 C1 antibody (Indoor Biotechnology, Deeside, U.K.) immobilised onto CNBr activated Sepharose 4B (Pharmacia, Milton Keynes, U.K.). The crude preparation was mixed with ~2 ml of the affinity resin for 2 h at 4° C. and then washed with 2–3 volumes of PBS. Elution of bound protein was carried out using 5 mM glycine containing 50% (v/v) ethylene glycol. Fractions (1–2 ml) were collected and neutralised with 0.8 ml of 0.2 M sodium phosphate buffer, pH 7.0. The fractions were pooled and dialysed overnight against 4 L PBS followed by a second dialysis against 2 L PBS for 2–3 h. The total protein was concentrated as required by ultrafiltration (MacroSep; Flowgen, U.K.).

This yielded protein of greater than 95% purity as judged by denaturing polyacrylamide gel electrophoresis in the presence of sodium dodecyl sulphate, C4 reverse phase high performance liquid chromatography (RP-HPLC) and high pressure size exclusion chromatography (HP-SEC) and no other contaiminating protease activity could be detected.

Inhibitors of Der p I

Using the purified Der p I it was surprisingly found that inhibitors to the enzyme could be made. These inhibitors are of the general formula

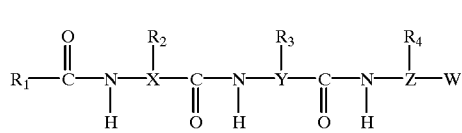

I where X, Y, and Z may be N or CH.

$R_1$ is a blocking group for the N-terminal amino acid nitrogen (T. Greene. Protective Groups In Organic Synthesis). $R_2$, $R_3$, and $R_4$ are side-chains on X, Y, and Z.

W is a group that reactions irreversibly with an active cysteine thiol of Der p I.

Where X and Y are CH, stereochemistry is exclusively of the "S" configuration, providing L -alpha-amino acid residues. Where Z is CH, the configuration may be "R" or "S" dependent upon W, but the chiral centre is derived stereospecifically with retention of configuration from the L -alpha-amino acid precursor. Where X, Y or Z are nitrogen, the residue is a peptidomimetic, an "azapeptide".

Preferably, $R_1$ represents an optionally substituted hydrophobic aryl or heteroaryl group optionally connected through a heteroatom (O, S, N, P) to the carbonyl. When connected through N or P the heteroatom may be mono or diaryl or mono or diheteroaryl substituted.

Alternatively, $R_1$ represents a hydrophobic aliphatic group of 3 carbons or more, linear or branched optionally connected through a heteroatom (O, S, N, P) to the carbonyl. When connected through N or P, the heteroatom may be mono or di-substituted.

These compounds can also be optionally substituted aryl for example optionally substituted phenyl, naphthyl or unsubstituted 2-naphthyl or 9-anthracyl. Additionally, optionally substituted phenyl may be uonsubstituted phenyl or phenyl having 1 to 5 fluoro substituents or phenyl having 1 to 3 substituents where the substituents are independently selected from the group which comprises lower alkyl, lower alkoxy, nitro, halo, acetyl, benzoyl, hydroxyl, amino, methylamino, —COOH, —CONH$_2$, —COOR$^2$, and NHCOR$^2$ wherein R$^2$ is lower alkyl.

Optionally substituted 1-naphthyl includes unsubstituted 1-naphthyl and 1-naphthyl substituted at the 2-position with lower alkyl, lower alkoxy or trifluoromethyl.

Optionally substituted heteroaryl includes optionally substituted, 5 or 6 membered aromatic group containing 1 to 4 heteroatoms chosen from O, S, N, a 1 or 2-naphthyl or a 9-anthracyl group which may contain 1 to 4 heteroatoms chosen from O, S, and N.

Most preferably $R_1$ represents pkhenyl, diphenyl amino radical, 9-xanthenyl, piperonyl, phenyl amino radical, tert-butoxy, CF$_3$-phenyl, a mono or disubstituted phenyl where the substituent is a lower alkyl C1–3, lower alkoxy C1–3, mono 2 or 3 amino or carboxy substituted phenyl, These criteria will also apply for diphenylamino radical and 9-xanthenyl. In addition, straight chain or branched aliphatics such as pivolyl, n-butyl and variants thereof upto C8.

Preferably $R_2$ represents a hydrophobic side-chain as found bonded to the C-alpha of commercially available amino acids. Hydrophobic refers to straight or branched chain alkyl (Methyl such as Ala); cyclohexylmethyl; 2-methylpropyl i.e. Leu; n-butyl i.e. Norleucine; 1-methylethyl i.e. Val; 1-methylpropyl i.e. Ile; 3-methylbutyl, i.e. homoleucine; ethyl i.e. Abu.

Alternatively, the hydrophobic chain may contain a heteroatom such as N, O, S such as 2-methylthioethyl (methionine), 4-aminobutyl i.e. Lys; or ethyl-2-carboamide i.e. Gln.

Alternatively, the hydrophobic chain may be a phenylmethyl radical optionally containing a nitrogen atom or be substituted on the phenyl ring with —OH, alkoxy, phenyl, or alkyl at C1–3.

Most preferably $R_2$ represents biphenylmethyl, 1-methylethyl i.e. valine; methyl i.e. alanine; or cyclohexylmethyl i.e. cyclohexylalanine.

Preferably $R_3$ represents a C1 alkyl group optionally substituted with a heteroatom, O, or F. Alternatively, $R_3$ may be 4-aminobutyl i.e. Lys; ethyl-2-carboxamide i.e. Gln; 2-(methylthiooxy) ethyl i.e. Met(O).

Most preferably, $R_3$ represents methyl i.e. alanine.

Preferably, $R_4$ represents a hydrophobic side-chain defined and with residues as described for $R_2$. In addition, 2-hydroxyethyl, i.e. Thr; or 2-fluoroethyl.

Most preferably $R_4$ represents 3-methylbutyl i.e. homoleu; cyclohexylmethyl i.e. cha; 2-methylpropyl i.e. leucine; or n-butyl i.e. norleucine.

Preferably W is selected from the group which comprises:

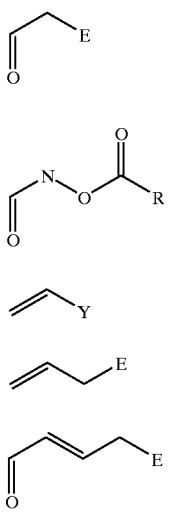

Preferably E is selected from the group which comprises:
i) OAr or SAr ii) 

iii) heteroaryl
iv) halogen v), vi), vii) 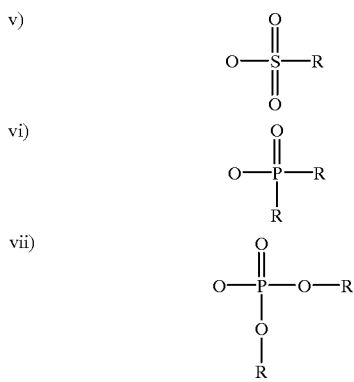

Preferably R is selected from the group which comprises alkyl and Ar.

Preferably Ar is selected from the group which comprises optionally substituted aryl of heteroaryl.

Preferably Y is selected from the group which comprises esters, sulphones, carboxylates, amides, phosphonates, ketones, sulfonates, nitriles, sulphonamides and nitro compounds.

DEFINITIONS

Optionally substituted aryl is preferably optionally substituted phenyl, benzyl or naphthyl. Optionally substituted phenyl is preferably unsubstituted phenyl or phenyl having 1 to 5 fluoro substituents or phenyl having 1 to 3 substituents where the substituents are independently selected form the group comprises lower alkyl, lower alkoxy, nitro, halo, acetyl, benzoyl, hydroxy, amino, methylamino, dimethylamino, diethylamino, methylthio, cyano, trifluoromethyl, phenylsulfonamidecarbonyl (—$CONHSO_2C_6H_5$), —COOH, —CONH, —COOR, NHCOR wherein $_2R$ is lower alkyl and 2,3,5,6,-tetramethyl-4-carboxy-phenyl (—$C_6H_5$ $(CH_3)_4$—COOH).

Optionally substituted 1-naphthyl includes unsubstituted 1-naphthyl and 1-naphthyl substituted at the 2-position with lower alkyl, lower alkoxy, or trifluoromethyl.

Halogen is preferably bromo, chloro or fluoro.

Alkyl is preferably a branched or unbranched, saturated aliphatic hydrocarbon radical, having the number of carbon atoms specified, or if no number is specified, having up to 8 carbon atoms. The prefix "alk—" is also indicative of a radical having up to 8 carbon atoms in the alkyl portion of that radical, unless otherwise specified. Examples of alkyl radicals include methyl, ethyl, n-propyl, iospropyl, n-butyl, tert-butyl, n-pentyl, n-hexyl, and the like. The terms "lower alkyl" and "alkyl of 1 to 4 carbon atoms" are, within the context of this specification, synonymous and used interchangeably.

Optional or optionally indicates that the subsequently described event or circumstance may or may not occur, and that the description includes instances where said event or circumstance occurs and instances in which it does not. For example, "optionally substituted phenyl" means that the phenyl radical may or may not be substituted and that the description includes both unsubstituted phenyl radicals and phenyl radicals wherein there is substitution.

These inhibitors were exemplified by the following examples which were produced as detailed.

Synthesis of Der p I Inhibitors

Potential inhibitors for Der p I were synthesised according to the general methods described below. Following synthesis the compounds were subjected to electrospray or MALDI-TOF mass spectrometry (MS) and the results are indicated.

Compound 1: N-Benzoyl-L-valyl-L-alanyl-L-norleucine

Solid phase benzoylated peptide synthesis.

Resin Loading (Step 1)

2-Chlorotritylchloride resin (4.9 g, 1.05 mmol/g, Novabiochem) was swelled in dichloromethane (40 ml) and a suspension of Fmoc-L-norleucine added and stirred for 5 minutes. A solution of diisopropylethylamine in DCM (10 ml, 57 mmol in 30 ml) was added over 5 minutes and the resulting mixture stirred at room temperature for 2 hours. Methanol (5 ml) added and reaction mixture stirred for a further 10 minutes before resin filtered and washed with 3×DCM, 2×DMF, 2×2-propanol, 2×DMF, 2×2-propanol, methanol, 2×ether and dried under vacuum for 24 hours.

Amino Acid Deprotection (Step 2)

Fmoc-L-norleucine loaded resin was deprotected by treatment with 20% piperidine in DMF over 4 hours. The swollen resin was filtered, washed with 5×DMF, 2×ether and dried under vacuum for 24 hours.

Peptide Chain Extension (Step 3)

L-Norleucine loaded resin (5 mmol) was added to a solution of Fmoc-L-alanine (6.23 g, 20 mmol), hydroxybenzotriazole (3.0 g, 20 mmol). 2-(1-H-benzotriazole-1-yl)-1,1,3,3-tetramethyluronium hexafluorophosphate (7.59 g, 20 mmol) and diisopropylethylamine (6.97 ml, 40 mmol) in DMF (20 ml) and allowed to swell over 4 hours with mild agitation. Resin was filtered and washed with 4×DMF, 2×ether and dried under vacuum overnight. Steps (2) and (3) were carried out repetitively with Fmoc-L-alanine and Fmoc-L-valine to afford resin bound tripeptide H-L-valyl-L-alanyl-L-norleucine.

Peptide Chain Benzoylation (Step 4)

L-Valyl-L-alanyl-L-norleucine loaded resin (1 g, approx. 1 mmol) was added to a solution of benzoic acid (0.488 g, 4 mmol), hydroxybenzotriazole (0.6 g, 4 mmol), 2-(1-H-benzotriazole-1-yl)-1,1,3,3-tetramethyluronium hexafluorophosphate (1.52 g, 4 mmol) and diisopropylethylamine (1.40 ml, 8 mmol) in DMF (5 ml) and allowed to sell over 6 hours with mild agitation. Resin was filtered and washed with 4×DMF, 2×ether and dried under vacuum overnight.

Resin Cleavage (Step 5)

N-Benzoyl-L-valyl-L-alanyl-L-norleucine loaded resin (1.0 g, appr. 1 mmol) was treated with a 1% solution of trifluoroacetic acid in dichloromethane (20 ml) containing triethylsilane (320 µl, 2 mmol) for 1 hour. Resin was removed by filtration and washed with dichloromethane (3×10 ml). Organic layer was collected, evaporated and triturated with ether to afford N-benzoyl-L-valyl-L-alanyl-L-norleucine (285 mg).

Electrospray MS m/z 407 [MH$^+$].

Compound 2

N-Benzoyl-L-valyl-L-alanyl-L-norleucine bromomethyl ketone

N-Benzoyl-L-valyl-L-alanyl-L-norleucine (140 mg, 0.34 mmol) was suspended in dry THF (3 ml) and dry DMF was added dropwise to afford homogeneity. The reaction mixture as cooled to −10° C. and isobutylchloroformate (129 µl, 1.0 mmol) and N-methylmorpholine (109 µl, 1.0 mmol) added with stirring under Argon. The mixture was stirred for 30 minutes before a solution of diazomethane in ether (5 ml, approx. 2 mmol) was added. The reaction mixture was allowed to warm to room temperature over 1 hour before a 1:1 solution of acetic acid and 50% HBr (1 ml, 3.0 mmol HBr) was added dropwise and stirred for 15 minutes. The organic phase was diluted with ethylacetate (40 ml), washed with water (10 ml), brine (10 ml) and sat. bicarbonate (2×10 ml), dried over MgSO$_4$ solvent removed under vacuum. This afforded an off white solid (152 mg) which could be further purified as required by preparative HPLC. Electrospray MS m/z 482 [MH$^+$] and 484 [MH$^+$].

Compound 3

N-Benzoyl-L-valyl-L-alanyl-L-norleucine 2,6-bis(trifluoromethyl)benzoyloxy methyl ketone A mixture of potassium fluoride (0.1 mmol, 6 mg) and 2,6-bis(trifluoromethyl)benzoic acid (0.066 mmol, 17 mg) in dry DMF (500 µl) was stirred over molecular sieves at room temperature for 5 minutes. A solution of N-benzoyl-L-valyl-L-alanyl-L-norleucine bromomethyl ketone (0.033 mmol), 16 mg) in dry DMF (500 µl) was added and the reaction mixture stirred for 1 hour. The reaction mixture was passed through a short silica plug and washed with 5% methanol in dichloromethane. Solvent was removed under vacuum and the residue purified using prep. HPLC. Freeze drying afforded (6.4 mg) as a white lyophilisate. Electrospray MS m/z 660 [MH$^+$].

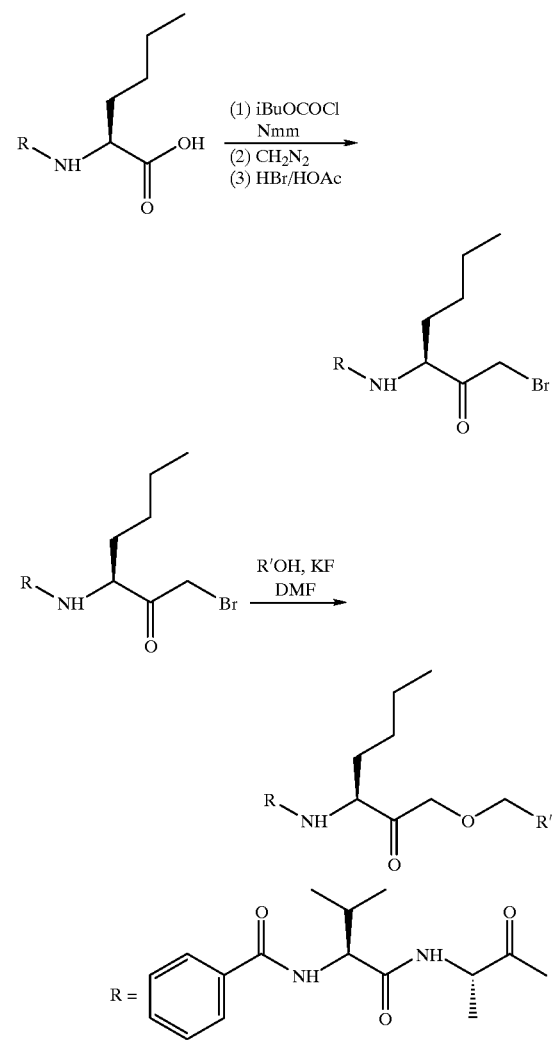

Similarly the following compounds were prepared.

Compound 4

N-Benzoyl-L-valyl-L-alanyl-L-norleucine 2,6-dimethyl benzoyloxy methyl ketone (Electrospray MS m/z 552 [MH$^+$]) from of N-benzoyl-L-valyl-L-alanyl-L-norleucine bromomethyl ketone and 2,6-dimethylbenzoic acid.

Compound 5

N-Benzoyl-L-valyl-L-alanyl-L-norleucine 2-hydroxybenzoyloxy methyl ketone (Electrospray MS m/z 540 [MH$^+$]) from of N-benzoyl-L-valyl-L-alanyl-L-norleucine bromomethyl ketone and 2-hydroxybenzoic acid.

Compound 6

N-Benzoyl-L-valyl-L-alanyl-L-norleucine 2,6-dichlorobenzoyloxymethyl ketone (Electrospray MS m/z 592 [MH$^+$] and 594 [MH$^+$]) from of N-benzoyl-L-valyl-L-alanyl-L-norleucine bromomethyl ketone and 2,6-dimethylbenzoic acid.

Compound 7

N-Benzoyl-L-valyl-L-alanyl-L-norleucine benzoyloxymethyl ketone (Electrospray MS m/z 524 [MH$^+$]) from of N-benzoyl-L-valyl-L-alanyl-L-norleucine bromomethyl ketone and benzoic acid.

Compound 8

N-Benzoyl-L-valyl-L-alanyl-L-norleucine 2,3,4,5,6-pentafluoro benzoyloxy methyl ketone (Electrospray MS m/z 614 [MH$^+$]) from of N-benzoyl-L-valyl-L-alanyl-L-norleucine bromomethyl ketone and 2,3,4,5,6-pentafluorobenzoic acid.

Compound 9

N-Benzoyl-L-valyl-L-alanyl-L-norleucine 1,1-dimethylpropyloxymethyl ketone (Electrospray MS m/z 504 [MH$^+$]) from of N-benzoyl-L-valyl-L-alanyl-L-norleucine bromomethyl ketone and 1,1-dimethylpropanoicacid.

Compound 10

N-Benzoyl-L-valyl-L-alanyl-L-norleucine N-(-benzyloxycarbonyl)-D-serinyl-(O-tert-butyl) oxymethyl ketone (Electrospray MS m/z 697 [MH$^+$]) from of N-benzoyl-L-valyl-L-alanyl-L-norleucine bromomethyl ketone and N-benzyloxycarbonyl-D-serinyl-O-tert-butylether.

Compound 11

N-Benzoyl-L-valyl-L-alanyl-L-norleucine N(-benzyloxycarbonyl)-D-serinyloxy methyl ketone (Electrospray MS m/z 641 [MH$^+$]) from of N-benzoyl-L-valyl-L-alanyl-L-norleucine bromomethly ketone and N-benzyloxycarbonyl-D-serine.

Compound 12

N-Benzoyl-L-valyl-L-alanyl-L-norleucine 2-furanoxy methyl ketone (Electrospray MS m/z 514 [MH$^+$]) from of N-benzoyl-L-valyl-L-alanyl-L-norleucine bromomethyl ketone and 2-furan carboxylic acid.

Compound 13

N-Benzoyl-L-valyl-L-alanyl-L-norleucine 2,6-dichlorophenylacyloxy methyl ketone (Electrospray MS m/z 606 [MH$^+$], 608 [MH$^+$]) from of N-benzoyl-L-valyl-L-alanyl-L-norleucine bromomethyl ketone and 2,6-dichlorophenylacetic acid.

Standard preparative HPLC conditions were used to analyse these compounds thus C4 preparative HPLC system (Vydac, 22×250 mm) eluting at 10 ml per minute a gradient of 5–95% (90% acetonitrile (0.1% TFA)) over 30 minutes.

Compound 14

N-Benzoyl amino-L-valyl-L-alanyl-L-norleucyl-hydroxamic acid

To a suspension of Bz-Val-Ala-norLeu-OH (50 mg, 0.12 mmol) in THF (5 ml) in a plastic reaction vessel was added diazomethane (0.3 mmol) in ether 1.5 ml. Gas evolution was observed and to the resulting clear solution was added acetic acid (0.05 ml) and the solution was evaporated to dryness. The residue was dissolved in methanol (2 ml) and hydroxylamine (2 mmol) in methanol (2 ml) was added and the solution stirred for 5 hours at room temperature. The solution was concentrated water added (2 ml), and the resulting solid was filtered and dried to yield 33 mg, 65%.

Compound 15

N-(Benzoyl amino-L-valyl-L-alanyl-L-norleucyl)-O-benzoyl hydroxamate

To a solution of Bz-Val-Ala-norLeu-NHOH (10 mg, 0.022 mmol) in dry pyridine at −10° C. was added benzoyl chloride (0.004 ml, 0.03 mmol) and stirred for 2 hours. The solution was evaporated and purified according to the method described in the preparation of Ethyl-(S)-(E)-3-((N-benzoyl valyl alanyl)amino-6-methyl-hept-2-enoate, collecting the peak elution at 25–27 min. and lyophilised to yield 0.5 mg, 5%.

Electrospray MS m/z 525 [MH$^+$].

Compound 16

N-(N-benzoyl-L-valyl-L-alanyl-L-norleucyl)-O-2,6-dimethyl-benzoyl hydroxamate

To a solution of 2,6-dimethylbenzoic acid (4 mg, 0.024 mmol) in dry DMF (1 ml) cooled to 0° C. was added 1-hydroxy-7-azabenzotriazole (3.2 mg, 0.023 mmol), O-7-azabenzotriazole-1-yl-1,1,3,3-tetramethyl uronium hexafluorophosphate (9 mg, 0.023 mmol) and N-methylmorpholine (0.008 ml, 0.07 mmol) and the solution was stirred for 5 minutes. The hydroxamic acid Bz-Val-Ala-norLeu-NHOH (10 mg, 0.02 mmol) was added and the reaction stirred overnight. The solution was evaporated and purified according to the method described in the preparation Ethyl-(S)-(E)-3-((N-benzoyl valyl alanyl) amino-6-methyl-hept-2-enoate collecting the peak eluting at 26–28 min. and lyophilised to yield 0.9 mg, 6%.

Electrospray MS m/z 553 [M$^+$+H], 575 [M$^+$Na]

Compound 17

Preparation of N,O-dimethyl(tert-butoxycarbonyl amino-L-leucyl)hydroxylamine

A solution of Boc-Leu-OH.H$_2$O (80.3 mmol) and N-methyl morpholine (88 mmol) in THF (35 ml) was added to a pre cooled solution of isobutyl chloroformate (88 mmol) in THF (65 ml) under nitrogen at between −10 and −15° C. over 40 minutes. The reaction was stirred at −10° C. for 1 hour after which time N-methyl morpholine (88 mmol) was added followed by N,O-Dimethylhydroxylamine hydrochloride (88 mmol) portion wise between −10 and 0° C. The reaction was then stirred at −10° C. for 1 hour and then allowed to warm up to room temperature over night. The THF was then removed under vacuum and water (50 ml) and ethylacetate (200 ml) added. The organic layer was then washed with 0.1 M citric acid solution (4×50 ml), then saturated sodium bicarbonate (4×50 ml), dried over magnesium sulphate and then concentrated under vacuum to give the product.

Compound 18

Preparation of N,O-dimethyl(amino-L-leucyl) hydroxylamine

Hydrogen chloride in dioxane (4M, 75 mL) was added to Boc-Leu-N(OMe)Me (33 mmol) with cooling and then

Compound 19

Preparation of N,O-dimethyl (tert-butoxycarbonyl amino-L-alanyl-L-leucyl) hydroxylamine A solution of Boc-Ala-OH (46 mmol) and N-methyl morpholine (46 mmol) in THF (20 ml) was added to a pre cooled solution of isobutyl chloroformate (46 mmol) in THF (30 ml) under nitrogen at between −10 and −15° C. over 30 minutes. The reaction was stirred at −10° C. for 1 hour after which time a solution of N-methyl morpholine (46 mmol) and HCl.H2N-Leu-N(OMe)Me (41.8 mmol) in 1,4-dioxane (20 ml) was added drop wise slowly. The reaction was left for 1 hour at −10° C. and then allowed to warm up to room temperature. After concentrating the solution under high vacuum, water (50 ml) and ethylacetate (200 ml) was added. The organic layer was then washed with 0.1 M citric acid solution (4×50 ml), then saturated sodium bicarbonate (4×50 ml), dried over magnesium sulphate and then concentrated under vacuum to give the product.

Compound 20

Preparation of N,O-dimethyl(amino-L-alanyl-L-leucyl)hydroxylamine

Hydrogen chloride in dioxane (4M, 80 mL) was added to Boc-Ala-Leu-N(OMe)Me (33 mmol) with cooling and then stirred at room temperature for 1.5 hour. The solution was then concentrated under vacuum. Diethyl ether (100 ml) was then added and concentrated down to dryness three times to give the product.

Compound 21

Preparation of N,O-dimethyl(tert-butoxycarbonyl amino-L-valyl-L-alanyl-L-leucyl)hydroxylamine A solution of Boc-Val-OH (46 mmol) and N-methyl morpholine (46 mmol) in THF (20 ml) was added to a pre cooled solution of isobutyl chloroformate (46 mmol) in THF (30 ml) under nitrogen at between −10 and −15° C. over 30 minutes. The reaction was stirred at −10° C. for 1 hour after which time a solution of N-methyl morpholine (46 mmol) and HCl.H2N-Ala-Leu-N(OMe)Me (41.8 mmol) in 1,4-dioxane (30 ml) was added drop wise slowly. The reaction was left for 1 hour at −10° C. and then allowed to warm up to room temperature. After concentrating the solution under high vacuum, water (50 ml) and ethylacetate (200 ml) was added. The organic layer was then washed with 0.1 M citric acid solution (3×50 ml), then saturated sodium bicarbonate (3×50 ml), dried over magnesium sulphate and then concentrated under vacuum to give the product.

Electrospray MS m/z 445 [MH$^+$]

Compound 22

Preparation of tert-butoxycarbonyl amino-L-valyl-L-alanyl-L-leucyl aldehyde

A solution of lithium aluminium hydride (4.5 mmol)in THF (24.5 mL) was cooled to between −15 and −10° C. Boc-Val-Ala-Leu-N(OMe)Me (2.2 mmol) in THF (10 mL) was then added very slowly to maintain the low temperature. After 40 minutes ethyl acetate (10 mL) was added slowly at −15° C. and then left for 10 minutes. Water (2 mL) was then added very slowly, again at −15° C. and the reaction then allowed to warm up to room temperature. Citric acid solution (100 mL, 0.5M) was then added and the product extracted into ethyl acetate. The ethyl acetate layer was washed with 100 ml saturated sodium bicarbonate solution, followed by 100 ml water and then dried over magnesium sulphate. The solution was then concentrated to give the product which was subsequently used crude.

Electrospray MS m/z 386 [MH$^+$]

Compound 23

Ethyl-(S)-(E)-3-((tert-butoxycarbonyl amino-L-valyl-L-alanyl) amino-6-methyl-hept-2-enoate To a suspension of sodium hydride (46 mg, 1.9 mmol) in anhydrous THF (4 ml) cooled to 0° C. was added a solution of triethylphosphonoacetate (420 mg, 1.9 mmol) in THF (2 ml) dropwise over 5 minutes and the mixture stirred until gas evolution ceased. The solution was added dropwise to a solution of Boc-Val-Ala-Leucyl aldehyde (600 mg, 1.56 mmol) in dry THF cooled to −10° C. The reaction mixture was stirred for 1 hour and saturated ammonium chloride (10 ml) was added. A white solid precipitated which was removed by filtration and the filtrate was partitioned between ethyl acetate and water. The organic layer was dried with magnesium sulphate and evaporated to give an oil which was crystallised from acetonitrile water to yield the title compound, 640 mg, 91%.

Electrospray MS m/z 456 [M$^+$+H], 356 [(M$^+$-$^t$BOC)+1]

Compound 24

(S)-(E)-3-((tert-butoxycarbonyl amino-L-valyl-L-alanyl) amino-6-methyl-hept-2-enoic acid Ethyl-(S)-(E)-3-((tert-butoxy carbonyl amino valyl alanyl) amino-6-methyl-hept-2-enoate (455 mg, 1 mmol) was dissolved in dioxane (10 ml) was water added followed by lithium hydroxide (126 mg, 3 mmol). The solution was stirred for 3 hours and 1M HCl aq was added until the pH reached neutrality. The dioxane was removed by rotary evaporation and the pH adjusted to 4 with 1M HCl aq. The title compound precipitated, filtered and washed with water to yield 420 mg, 98%.

Electrospray MS m/z 428 [M$^+$+H]

Compound 25

1,1,1-Trifluoroethyl-(S)-(E)-3-((tert-butoxycarbonyl amino-L-valyl-L-alanyl) amino-6-methyl-hept-2-enoate The acid (Boc-Val-Ala-Leu-OH) (50 mg, 0.117 mmol) and dimethylaminopyridine (29 mg, 0.24 mmol) was dissolved in dry dichloromethane (1 ml) and cooled to 0° C. Water soluble carbodiimide hydrochloride salt (26 mg, 0.13 mmol) in 0.5 ml dichloromethane was added and the solution stirred for 5 minutes, 1,1,1-Trifluoroethanol (0.017 ml, 0.23 mmol) in 0.5 ml dichloromethane was added and the reaction was allowed to warm to room temperature after 1 hour and the reaction mixture stirred overnight. The reaction mixture was washed 2×2 ml 0.5M citric acid solution, 1×2 ml water, 1×2 ml saturated sodium bicarbonate solution, 1×2 ml water, dried with magnesium sulphate and evaporated to dryness to give the title compound Electrospray MS m/z 510 [M$^+$+H], 410 [(M$^+$-$^t$BOC)+1], 454 [(M$^+$-$^t$Bu)+1]

Compound 26

Ethyl-(S)-(E)-3-((N-benzoyl-L-valyl-L-alanyl) amino-6-methyl-hept-2-enoate

The Ethyl-(S)-(E)-3-((tert-butoxycarbonyl amino valyl alanyl) amino-6-methyl-hept-2-enoate (16.6 mg, 0.036 mmol) was dissolved in 4.0M HCl in dioxane (2 ml) stirred at room temperature for 30 minutes and evaporated to dryness. The residue was dissolved in DMF (0.5 ml) and N-methylmorpholine (7.36 mg, 0.073 mmol) added followed by benzoyl chloride (5.4 mg, 0.038 mmol) in DMF 0.5 ml. The reaction stirred for 2 hours, diluted with 0.1% trifluoroacetic acid solution (4 ml) and acetonitrile (2 ml) and injected onto a C4 preparative HPLC system (22×250 mm) eluting at 10 ml per minute, monitoring at 215 nm and a gradient of 10–90% system B over 25 minutes and holding at 90% for 15 minutes. System A=0.1% TFA in water, system B=90% acetonitrile, 10% system A. The peak eluting at 26–28 minutes was collected and lyophilised to a white solid, yield 4.5 mg, 27%.

Electrospray MS m/z 460 [M$^+$+H]

In an identical manner to the above, the following compounds were prepared:

Compound 27

Ethyl-(S)-(E)-3-((2-trifluoromethyl-N-benzoyl-L-valyl-L-alanyl) amino-6-methyl-hept-2-enoate A yield of 3.7 mg, at 22% was obtained. Electrospray MS m/z 528 [M$^+$+H].

Compound 28

Ethyl-(S)-(E)-3-((Piperonyloyl amino-L-valyl-L-alanyl) amino-6-methyl-hept-2-enoate yield 3.8 mg, 23%.
Electrospray MS m/z 504 [M$^+$+H].

Compound 29

Ethyl-(S)-(E)-3-((Phenyl carbamoyl amino-L-valyl-L-alanyl) amino-6-methyl-hept-2-enoate As per method above, except that phenyl isocyanate was used in place of an acid chloride, yield 1.5 mg, 10%.
Electrospray MS m/z 475 [M$^+$+H].

Compound 30

Ethyl-(S)-(E)-3-((Diphenyl carbamoyl amino-L-valyl-L-alanyl) amino-6-methyl-hept-2-enoate yield 2.3 mg, 13%.
Electrospray MS m/z 551 [M$^+$+H].

Compound 31

Ethyl-(S)-(E)-3-((Naphthoyl amino-L-valyl-L-alanyl) amino-6-methyl-hept-2-enoate yield 1 mg, 6%.
Electrospray MS m/z 510 [M$^+$+H].

Compound 32

Ethyl-(S)-(E)-3-((Quinazoloyl amino-L-valyl-L-alanyl) amino-6-methyl-hept-2-enoate yield 1.5 mg, 9%.
Electrospray MS m/z 512 [M$^+$+H].

Compound 33

Ethyl-(S)-(E)-3-((Morpholinoyl amino-L-valyl-L-alanyl) amino-6-methyl-hept-2-enoate yield 2.9 mg, 19%.
Electrospray MS m/z 469 [M$^+$+H].

Compound 34

Ethyl-(S)-(E)-3-((Xanthene-9-oyl amino-L-valyl-L-alanyl) amino-6-methyl-hept-2-enoate As per method above, except that xanthane-9-carboxylic acid (8.1 mg, 0.036 mmol) was used in place of the acid chloride. Coupling of this acid was effected using 2-(1H-benzotriazole-1-yl)-1,1,3,3-teramethyluronium hexafluorophosphate (13.6 mg, 0.036 mmol), as activator and 1-hydroxybenzotriazole (5.5 mg, 0.036 mmol) as catalyst in the presence of N-methylmorpholine (10.8 mg, 0.108 mmol).

Yield 1.7 mg, 9%.
Electrospray MS m/z 564 [M$^+$+H].

Compound 35

Diethyl Phenylsulfonylmethylphosphonate (Adapted from I. Shahak, J. Almog, *Synthesis* 145 (1970).) The commercially available diethyl phenylthiomethylphosphonate (1.0 ml, 4.1 mmol) was dissolved in dichloromethane (10 ml). Sulphuric acid (10 ml, 25%) was added and the mixture cooled in ice. Solid Potassium permanganate was then added portionwise (3×0.5 g) with stirring after which time the reaction appeared to be complete. Solid sodium metabisulfite was added slowly until the mixture turned colourless. This was then extracted with ethyl acetate (×3) and the combined organic washings washed with saturated sodium bicarbonate solution followed by brine before drying over sodium sulphate. The volatiles were then removed in vacuo. The residue was purified by flash chromatography on silica eluting initially with ethyl acetate/hexane 8/2 followed by pure ethyl acetate. In this way the desired product, diethyl phenylsulfonylmethylphosphonate (1.0 g, quant) was obtained as a colourless solid.

MS (MALDI-TOF): required (M$^+$ (C$_{11}$H$_{17}$O$_5$PS)+1)= 292; obtained (M$^+$+1)=292

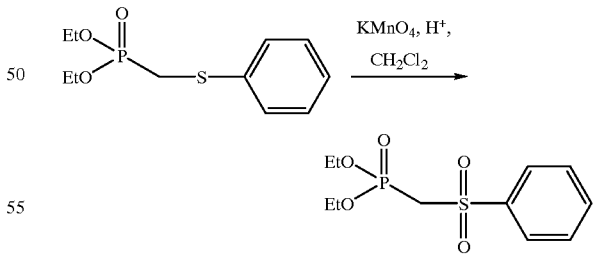

Compound 36

(S)-(E)-3-((tert-butoxycarbonylamino-L-valyl)-L-alanyl)amino-1-phenylsulfonyl-5-methyl-1-hexene Diethyl phenylsulfonylmethylphosphonate (38 mg, 129 mmol) was dissolved in dry THF (10 ml) and then cooled to 0° C. under an atmosphere of nitrogen. Sodium hydride (8 mg of 60% dispersion in oil, 200 mmol) was added and the mixture stirred for 15 mins (effervescence). The aldehyde 'Boc-Val-Ala-Leucyl aldehyde (50 mg, 129 mmol) was then added to the resulting solution and the mixture was stirred for 60 mins. The reaction was quenched by addition of dilute hydrochloric acid (0.1 M), followed by extraction with ethyl acetate (×3). The separated organic phase was sequentially washed with saturated sodium bicarbonate solution and brine before drying over sodium sulphate. The volatiles were removed in vacuo. The residue was purified by flash chromatography on silica eluting with ethyl acetate/hexane 4/6. An unidentified by-product was eluted first (12 mg) followed by the desired product (S)-(E)-3-(tert-butoxycarbonyl-amino-L-valyl-L-alanyl)amino-phenylsulfonyl-5-methyl-1-hexene (22 mg, 32%) as a solid.

Electrospray MS m/z 546 [M⁺+Na], 424 [(M-'Boc)+1]

Compound 38

(S)-(E)-3-((tert-butoxycarbonylamino-L-valyl)-L-alanyl)amino-1-methylsulfonyl-5-methyl-1-hexene Diethyl methylsulfonylmethylphosphonate (30 mg, 130 mmol) was dissolved in dry THF (5 ml) and then cooled to 0° C. under an atmosphere of nitrogen. Sodium hydride (7 mg of 60% dispersion in oil, 175 mmol) was added and the mixture stirred for 15 mins (effervescence). The aldehyde 'Boc-Val-Ala-Leucyl aldehyde (50 mg, 129 mmol) was then added to the resulting solution and the mixture then stirred for 60 mins. The reaction was quenched by addition of dilute hydrochloric acid (0.1 M), followed by extraction with ethyl acetate(×3). The separated organic phase was sequentially washed with saturated sodium bicarbonate solution and

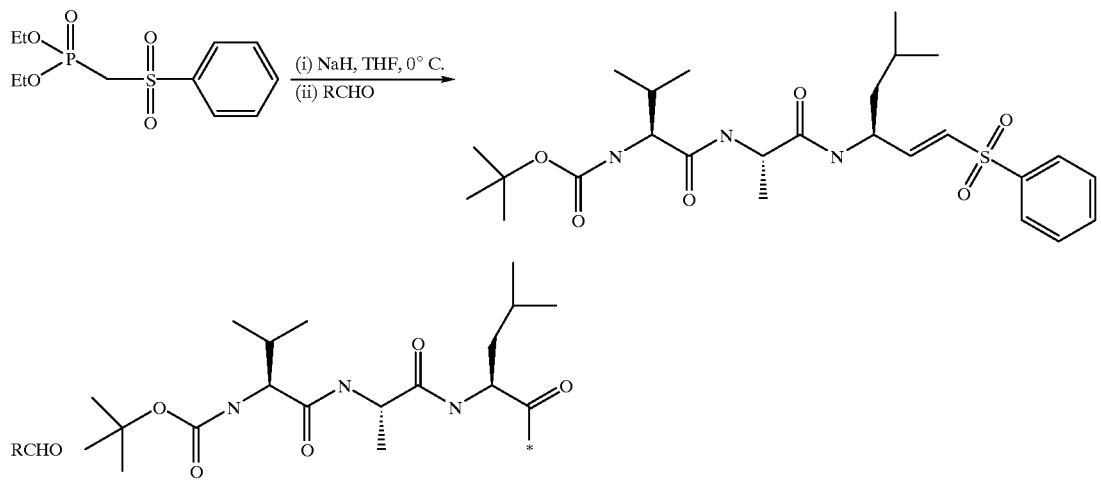

Compound 37

Diethyl Methylsulfonylmethylphosphonate

The commercially available Diethyl methylthiomethylphosphonate was converted to the title compound using the method of I. Shahak and J. Almog, *Synthesis* 171 (1969).

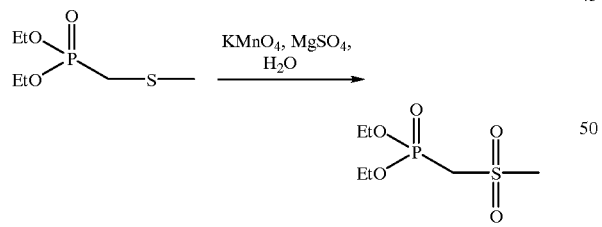

brine before drying over sodium sulphate. The volatiles were then removed in vacuo. The residue was purified by flash chromatography on silica eluting with ethyl acetate/hexane 8/2. An unidentified by-product was eluted first (4 mg) followed by the desired product (S)-(E)-3-((tert-butoxycarbonylamino-valyl)alanyl)amino-methylsulfonyl-5-methyl-1-hexene (24 mg, 40%) as a solid.

Electrospray MS m/z 484 [M⁺+Na], 362 [(M-' Boc)+1]

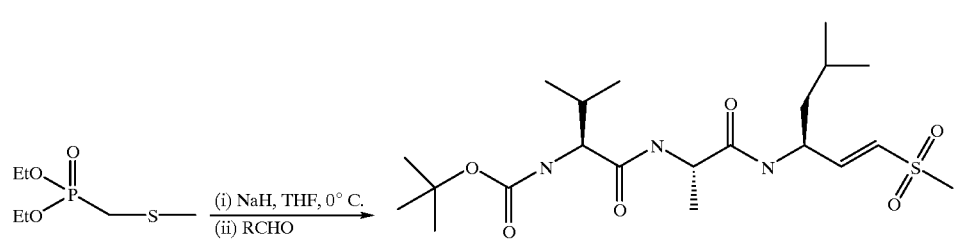

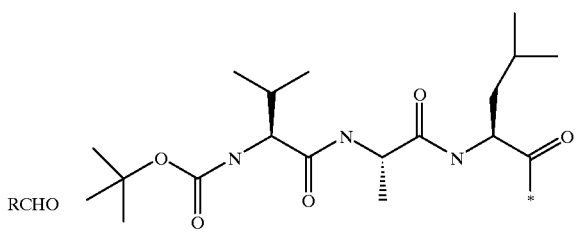

Compound 39

Ethyl Diethylphosphorylmethylsulfonate

Prepared in accordance with procedure B in L. Ghosez et. al. *Tetrahedron* 43 5125 (1987).

Electrospray MS m/z 261 [M$^+$+H], 283 [M$^+$+Na].

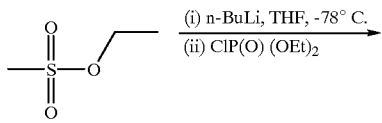

0° C. under an atmosphere of nitrogen. Sodium hydride (8 mg of 60% dispersion in oil, 200 mmol) was added and the mixture stirred for 15 mins (effervescence). The aldehyde $^t$Boc-Val-Ala-Leucyl aldehyde (50 mg, 129 mmol) was added to the resulting solution and the mixture stirred for 30 mins. The reaction was quenched by addition of dilute hydrochloric acid (0.1 M), followed by extraction with ethyl acetate (×3). The separated organic phase was sequentially washed with sodium bicarbonate solution and brine before drying over sodium sulphate. The volatiles were then removed in vacuo. The residue was purified by flash chromatography on silica eluting with ethyl acetate/hexane 1/1. The desired product, Diethyl(S)-(E)-3-((tert-butoxycarbonylamino-valyl)alanyl)amino-5-methylhexenyl sulfonate, (22 mg, 35%) was obtained as a solid.

electrospray MS m/z 492 [M$^+$+1], 392 [(M$^+$–$^t$Boc)+1]

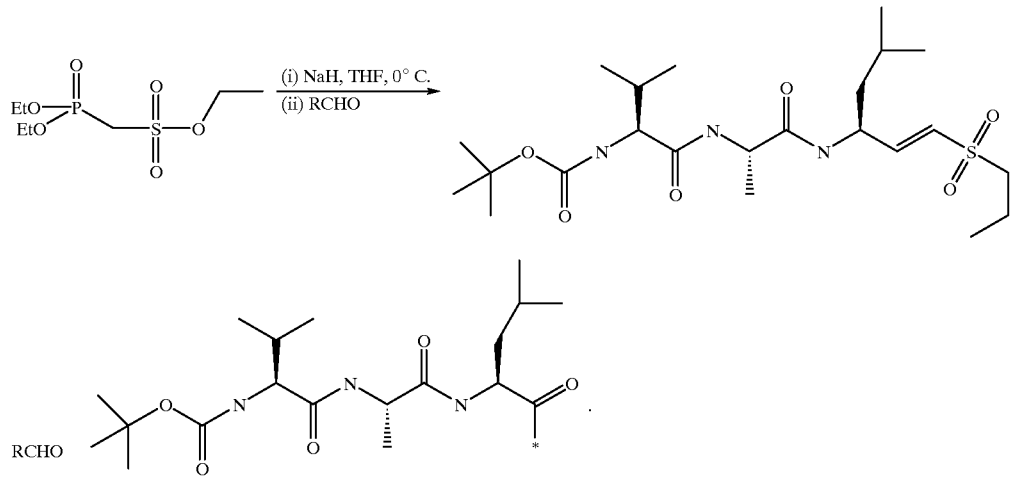

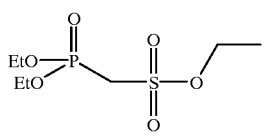

Compound 40

Ethyl(S)-(E)-3-((tert-butoxycarbonyl amino-L-valyl)-L-alanyl)amino-5-methylhexenylsulfonate.

Ethyl diethylphosphorylmethanesulfonate (36 ml, ~138 mmol) was dissolved in dry THF (5 ml) and then cooled to Determination of Kinetic Constant For Der-p I Substrates All Der-p I enzyme assays were routinely carried out in 50 mM potassium phosphate; pH 8.25 containing 1 mM ethylenediaminetetraaceticacid (EDTA) and 1 mM dithiothreitol (DTT). Product formation was monitored with respect to time by measuring the increase in fluorescence emission at 420 nm and exciting at 320 nm. All assays were carried out at 25° C. Stock solutions of the various substrates and/or inhibitors were made up in 100% dimethylsulphoxide (DMSO).

The kinetic constants ($K_M$ and $k_{cat}$) were calculated from the initial velocities of the enzymatic reaction at various substrate concentrations. These data were fitted, by regression analysis, to the Michaelis-Menten equation and the kinetic constants obtained.

Inactivation Kinetics

Scheme 1

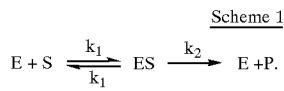

Scheme 2

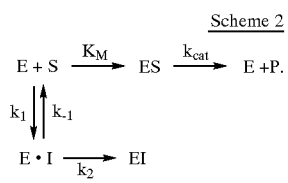

The reaction of enzyme and inhibitor is comprised of two steps. The first is binding of enzyme and inhibitor to produce the enzyme inhibitor complex (E.I). This step is assumed to be rapid and reversible, relative to the other steps, and no chemical reaction occurs. In this case $k_1$ is the second order rate constant for the formation of the E.I complex and $k_{-1}$ is the first order rate constant for the breakdown of the E.I. The second step in the process, occurring at a rate $k_2$, is the formation of the enzyme-inhibitor covalent complex (EI) resulting in irreversible inactivation of the enzyme.

The practice of inactivation kinetics of enzymes have been described by two standard accepted methods (Schemes 1 and 2). The first (Scheme 1) is the dilution method described by Kitz, C. G. and Wilson, I. B., (1962), *J. Biol. Chem.*, 237, 3245–3249. In this case enzyme and inhibitor are pre-incubated for a set period of time prior to quenching of this reaction by the addition of an excess of substrate. The second method (Scheme 2), is monitoring enzyme inactivation in the presence of substrate and irreversible inhibitors. This method has been described previously (Tian, W. -X. & Tsou, C. -L, (1982), *Biochemistry*, 21, 1028–1032; Morrison, J. F. & Walsh, C. T., (1988), *Adv. Enzymol. Relat. Areas Mol. Biol.*, 61, 201–301) and the equations describing the kinetics are shown below (Eq. 1, 2 and 3). In both cases the inhibitor concentration employed is at least 10 times greater than the enzyme concentration in order to maintain pseudo-first order conditions.

$$k_{app}=k_2[I]/1+[S]/K_M[I]+K_1) \qquad \text{Eq. 1}$$

$$[\text{Product}]=v_s t+(v_0-v_s)[1-\exp(-k_{app}t)]/k_{app}+d \qquad \text{Eq. 2}$$

$$\text{second order rate constant}=(k_{app}/[I])(1+[S]/K_M) \qquad \text{Eq. 3}$$

The apparent inactivation rate constant ($k_{app}$) was calculated using Eq. 2; where $v_o$ is the initial velocity of the reaction, $v_s$ is asymptotic steady-state velocity of the reaction, d is the intercept at time zero. The second order rate was calculated using Eq. 3.

Inhibition Kinetics of Der-p I

Assays were routinely carried out in 50 mM potassium phosphate; pH 8.25 containing 1 mM ethylenediaminetetraaceticacid (EDTA) and 1 mM dithiothreitol (DTT). The fluorogenic substrate was 2-aminobenzoylvalylalanylnorleucylseryl-(3-nitro)tyrosinyl aspartylamide. Product formation was monitored with respect to time by measuring the increase in fluorescence emission at 420 nm and exciting at 320 nm. Assays were carried out at 25° C. Stock solutions of the various inhibitors were made up in 100% dimethylsulphoxide.

Inactivation kinetics for various inhibitors were carried out using the techniques already described. In the dilution method, generally 100 nM Der p I was mixed and incubated with 0.5–10 uM of the inhibitor and aliquots were taken out at given time points (sampling time) and the residual enzyme activity determined by a ten-fold dilution into assay buffer containing saturating amounts of substrate. The residual activity was related to the sampling time and the curve fitted by computational non-linear least square regression analysis. In cases where the second order rate constants were greater than $10^5 M^{-1} s^{-1}$, second order conditions were employed (i.e. equimolar amounts of enzyme and inhibitor). Generally stoichiometric amounts of enzyme and inhibitor were incubated for given time intervals (sampling time) and the reaction stopped by a ten-fold dilution of this mixture by saturating amounts of substrate in assay buffer. A plot of reciprocal enzyme concentration versus sampling time was fitted by linear least square regression analysis to obtain the second order inactivation rate constant.

In cases where inactivation kinetics were calculated in the presence of enzyme, inhibitor and substrate the following conditions were employed. Generally a solution containing 12.5 mM substrate and 0.1–10 mM inhibitor was incubated at 25° C. for 5 min. prior to addition of enzyme (10 nM) to initiate the reaction. In the absence of inhibitor, product formation was linear with time. Inactivation of enzyme was exhibited by the downward curvature in the increase in fluorescence. The apparent inactivation rate constant ($k_{app}$) was determined by fitting these curves to Eq. 2, using least square regression analysis, and the second order rate constant determined using Eq. 3.

Assay Results

| Compound number | $k_{obs}/[I]$ ($M^{-1}s^{-1}$) |
|---|---|
| 3 | $>10^7$ |
| 4 | $1.6 \times 10^7$ |
| 6 | $6.8 \times 10^7$ |
| 7 | $3.7 \times 10^5$ |
| 8 | $>10^7$ |
| 9 | $2.3 \times 10^4$ |
| 10 | $1.9 \times 10^5$ |
| 11 | $1.2 \times 10^6$ |
| 12 | $1.9 \times 10^5$ |
| 13 | $6.6 \times 10^5$ |
| 15 | $1.5 \times 10^5$ |
| 16 | $1.6 \times 10^4$ |
| 23 | $1.7 \times 10^3$ |
| 25 | $3.1 \times 10^3$ |
| 26 | $4.1 \times 10^3$ |
| 27 | $6.3 \times 10^3$ |
| 28 | $6.8 \times 10^3$ |
| 29 | $4.6 \times 10^3$ |
| 30 | $7.5 \times 10^3$ |
| 34 | $1.1 \times 10^4$ |
| 36 | $6.4 \times 10^3$ |
| 38 | $1.1 \times 10^3$ |
| 40 | $6.9 \times 10^4$ |

Compounds for which no inhibition data is shown were key intermediates in the formation of further compounds or were too unstable to be tested and hence were intermediates to more stable compounds.

Pharmacophore Definition and Specification

A collection of compounds with biological activity for Der p I was provided as a training set. Each compound in the training set was subjected to full conformational analysis (J. Comp. Chem., 1995, 16, 171–187). A representative number of conformers were generated over a given energy range above the lowest energy conformation (J. Chem. Inf. Comp. Sci., 1995, 35, 285–294 and J. Chem. Inf. Comp. Sci., 1995, 35, 295–304).

This information was used to derive a pharmacophore (based on seven chemical feature type rules) (J. Chem. Inf. Comp. Sci., 1994, 34, 1297–1308) that correlates to the observed biological activity. It was assumed that the molecules in the training set all act at the same target in the same manner of action.

A pharmacophore consisting of at least the following chemical features defines the chemical motif of potential inhibitors of Der p I:

A Hydrogen bond acceptor feature, three Hydrophobe (J. Comp. Chem., 1986, 7, 565–577) features and a Hydrogen bond donor feature.

A Hydrogen bond acceptor feature matches the following atom types or groups of atoms which are surface accessible.

sp or $sp^2$ nitrogens that have a lone pair of electrons and a charge less than or equal to zero $sp^3$ oxygens or sulphurs that have a lone pair of electrons and charge less than or equal to zero non-basic amines that have a lone pair of electrons.

A Hydrogen bond donor feature has the same chemical rules, i.e. it matches the same atoms or groups of atoms, as the Hydrogen bond acceptor except that it also includes basic nitrogen. There is no exclusion of electron-deficient pyridines and imidazoles. This feature matches the following atom types or groups of atoms.

non-acidic hydroxyls thiols acetylenic hydrogens

NH moieties (except tetrazoles and trifluoromethyl sulfonamide hydrogens).

A Hydrophobe feature is defined as a contiguous set of atoms that are not adjacent to a concentration of charge (charged atoms or electronegative atoms), in a conformation such that the atoms have surface accessibility, including phenyl, cycloalkyl, isopropyl and methyl. This may also include residues which have a partial hydrophobic character such as Lysyl or Glutaminyl amino acid side-chains.

The term "pharmacophore" used herein is not meant to imply any pharmacological activity. The term refers to chemical features and their distribution in three-dimensional space which constitute and epitomise the preferred requirements for molecular interaction with a receptor. For example the receptor may be the catalytic active site of the cysteine protease Der p I.

Figure 4:
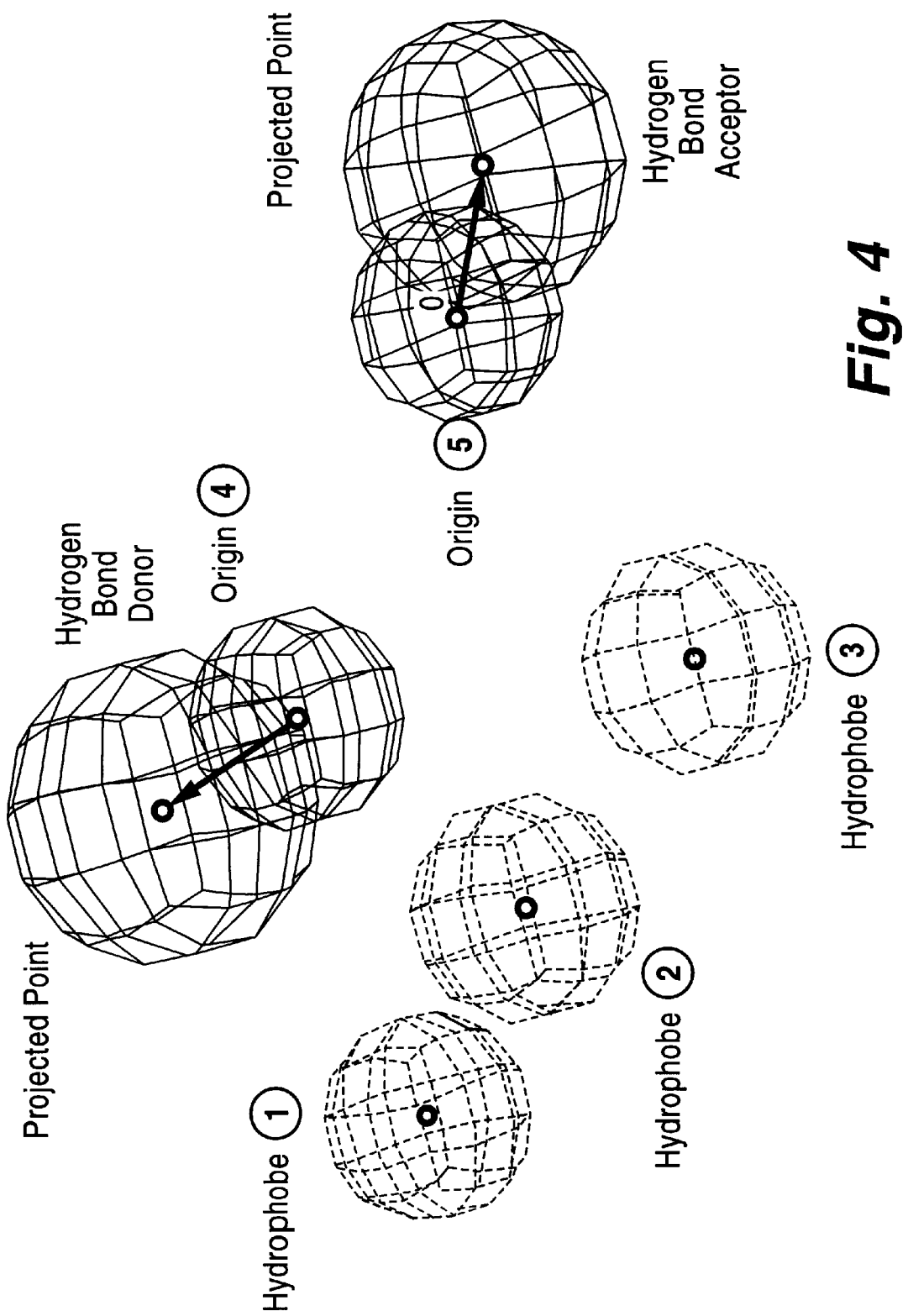
FIG. 4 shows the pharmacophore of the cysteinyl protease Der p I.
Figure 5:
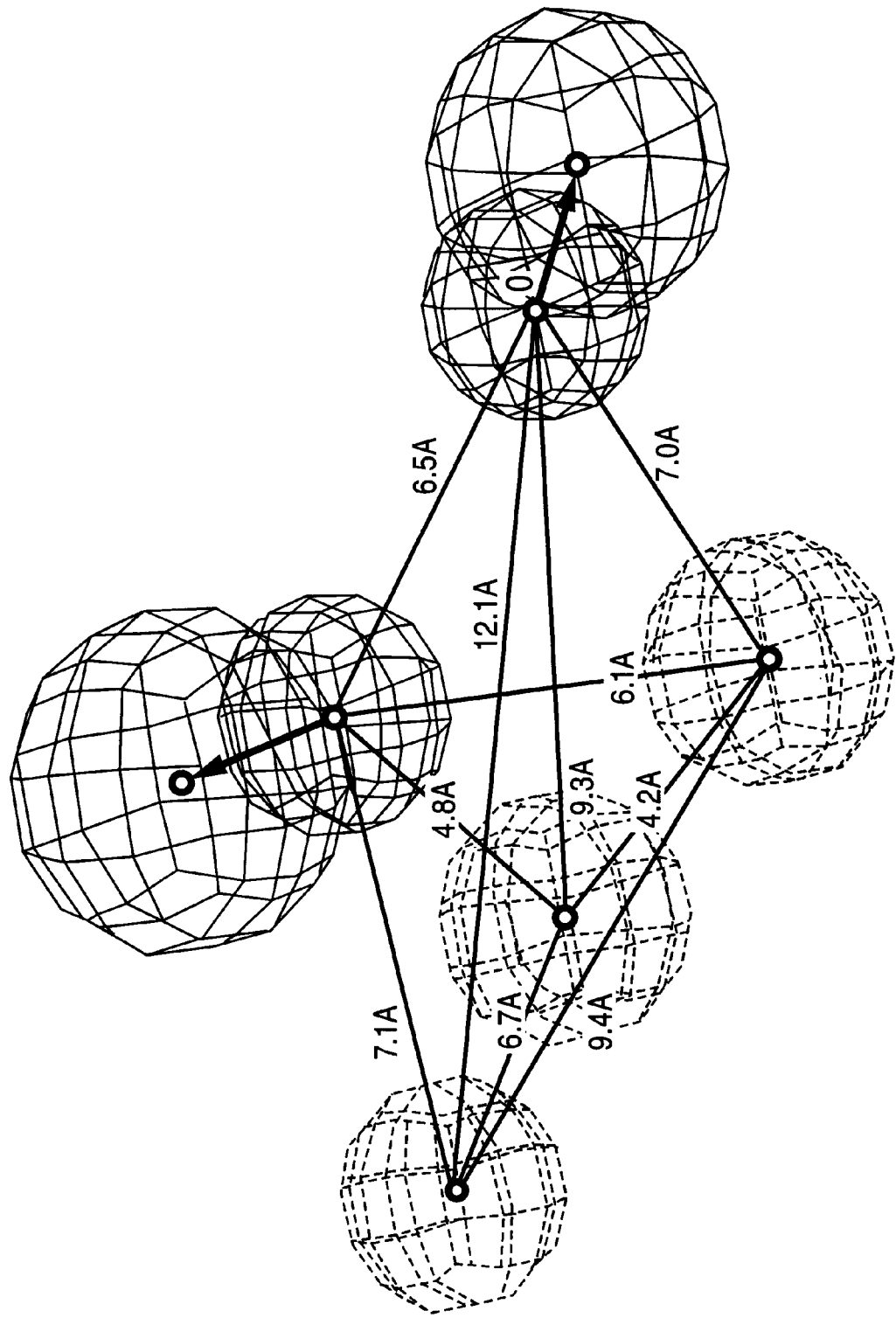
FIG. 5 shows the distance constraints of the pharmacophore of FIG. 4.
Figure 6:
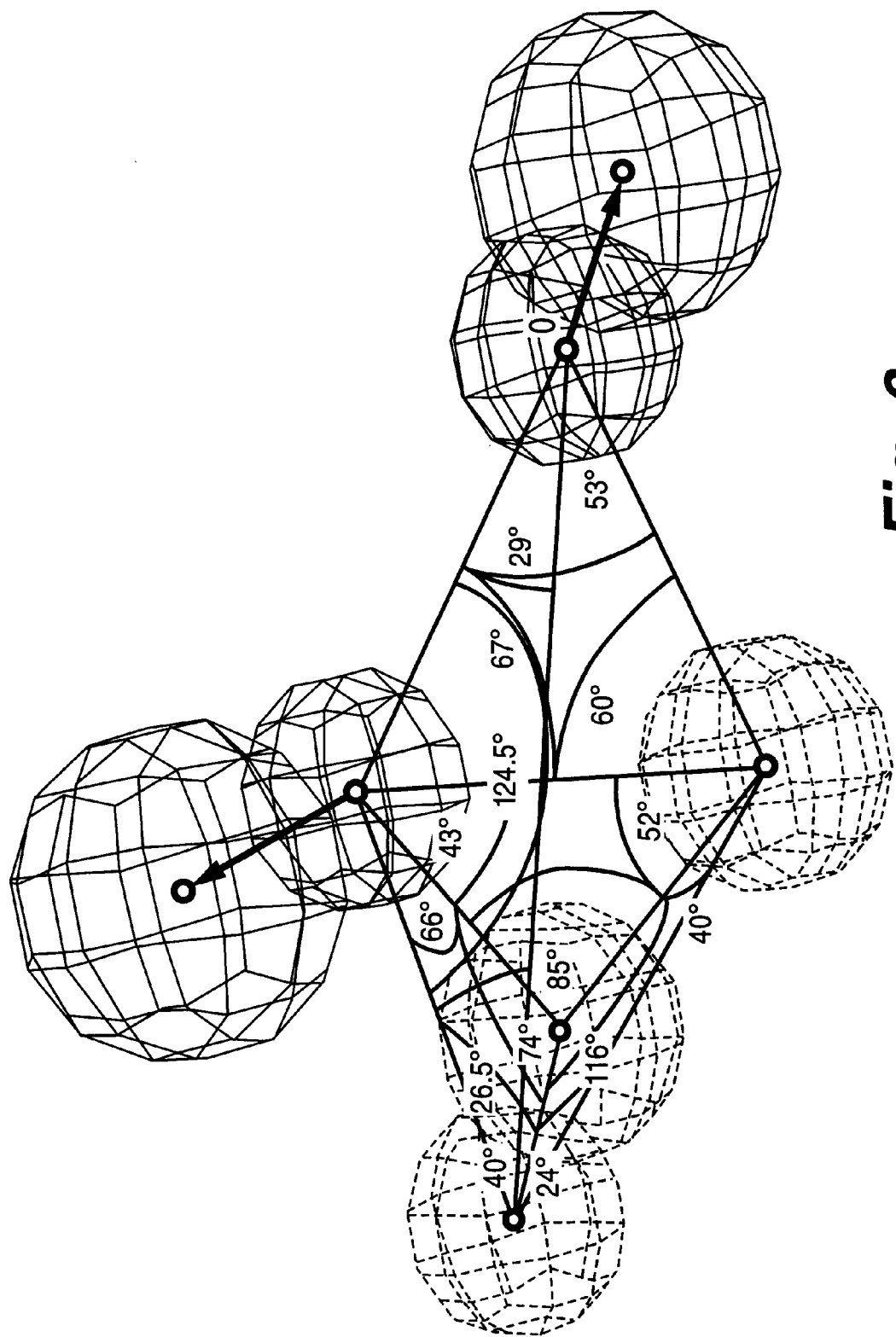
FIG. 6 shows the angle constraints of the pharmacophore of FIG. 4.
Figure 7:
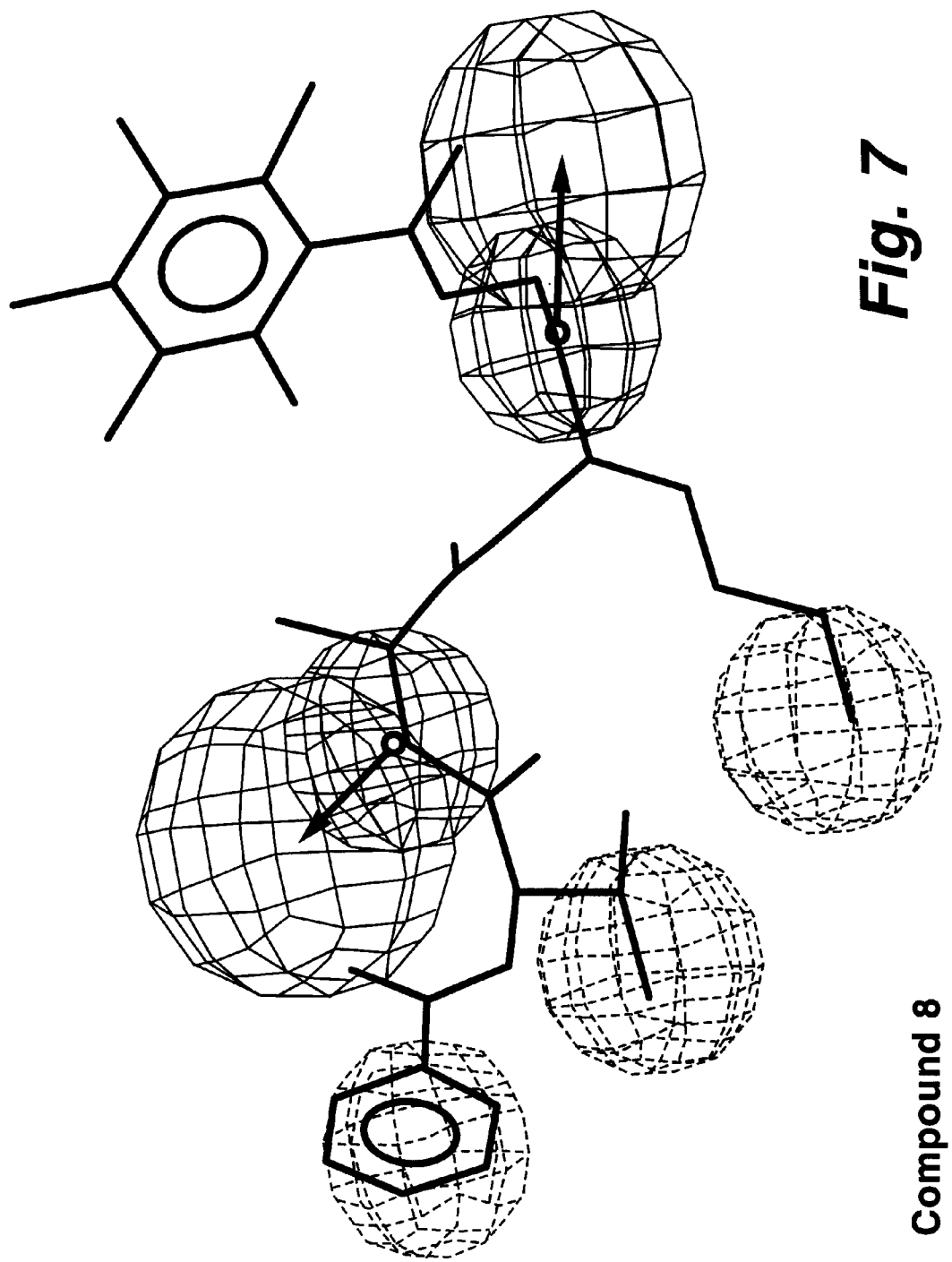
FIG. 7 shows the pharmacophore and illustrates how compound 8 fits the pharmacophore.
Figure 8:
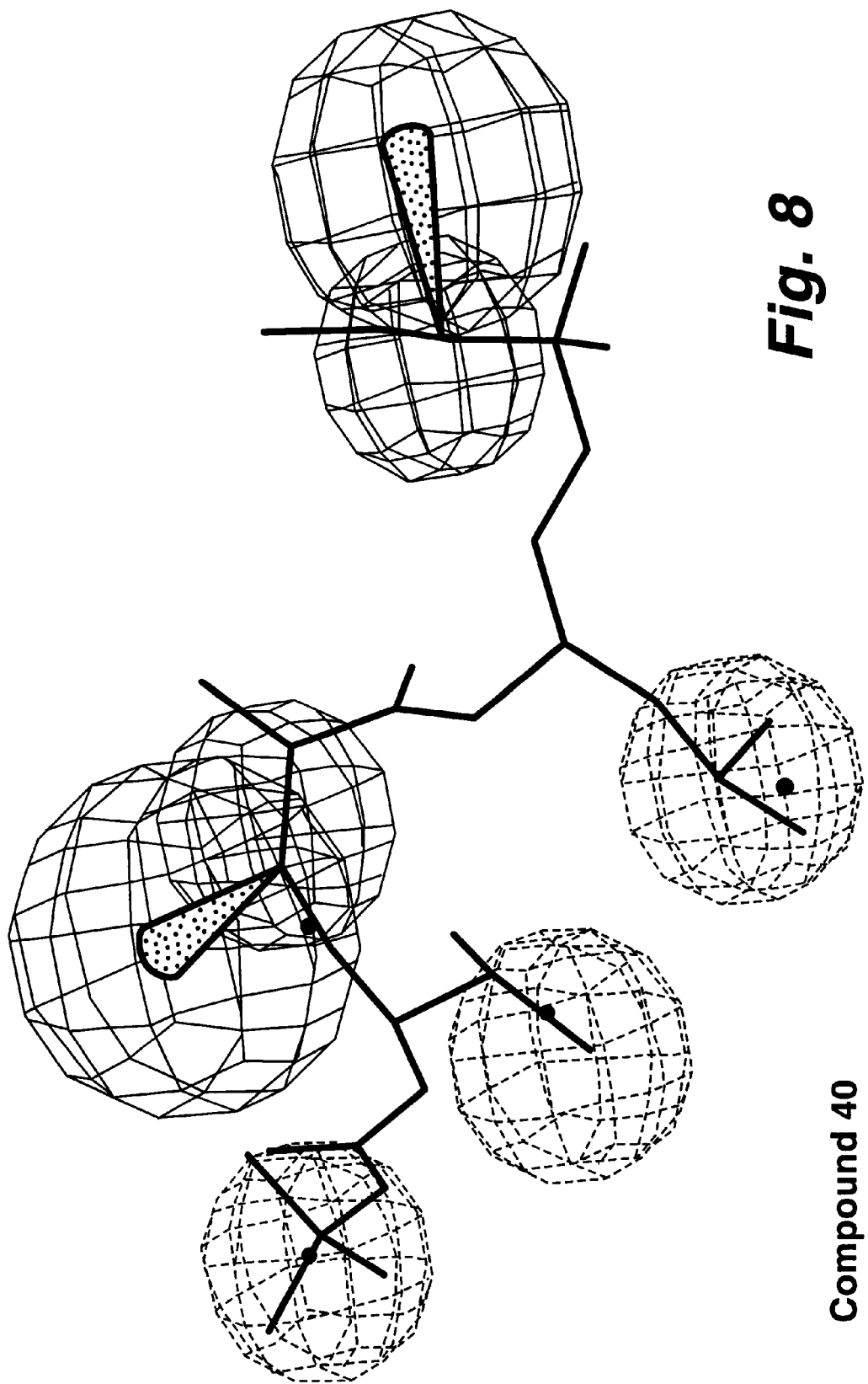
FIG. 8 shows the pharmacophore and illustrates how compound 40 fits the pharmacophore.
Figure 9:
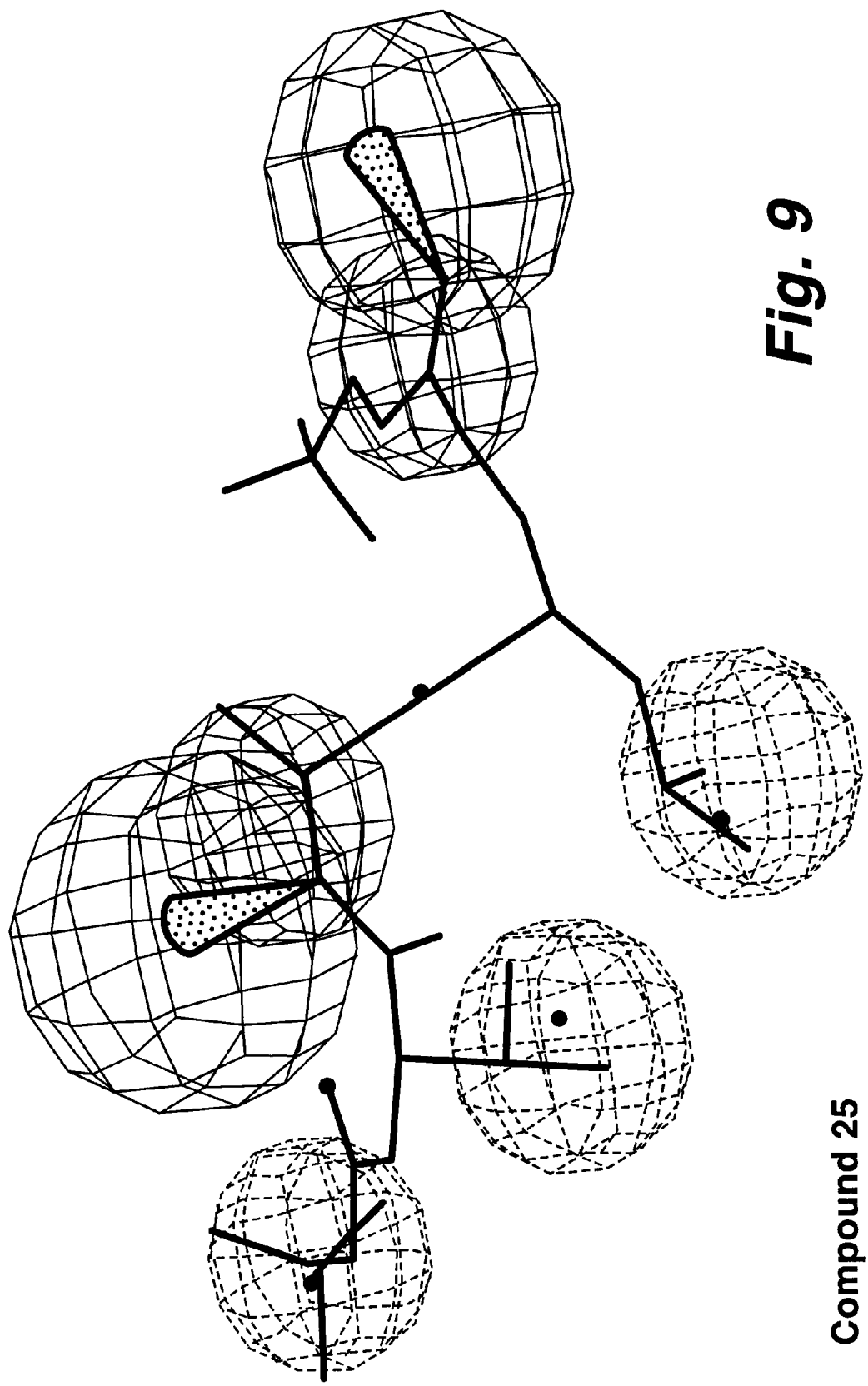
FIG. 9 shows the pharmacophore and illustrates how compound 25 fits the pharmacophore.
Figure 11:
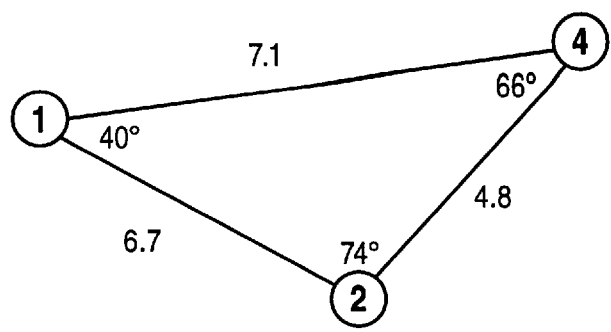
FIG. 11 shows the distance and angle constraints between points 1–2–4 of the pharmacophore of FIG. 4
Figure 10:
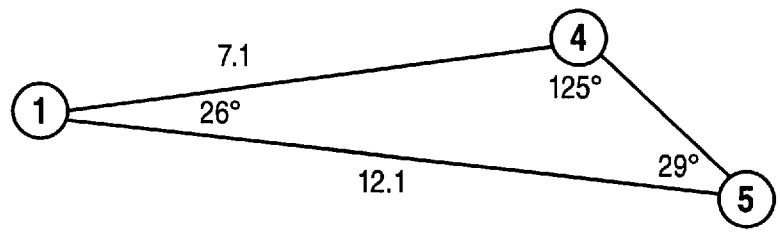
FIG. 10 shows the distance and angle constraints between points 1–4–5 of the pharmacophore of FIG. 4.
Figure 13:
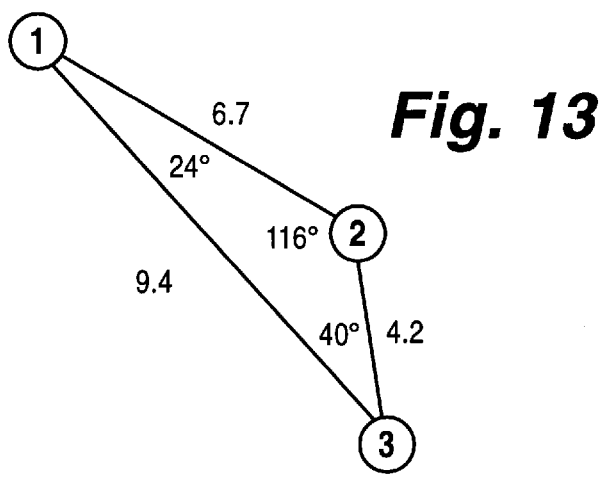
FIG. 13 shows the distance and angle constraints between points 1–2–3 of the pharmacophore of FIG. 4.
Figure 12:
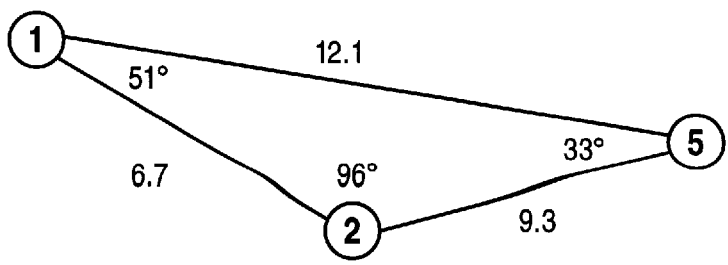
FIG. 12 shows the distance and angle constraints between points 1–2–5 of the pharmacophore of FIG. 4.
Figure 18:
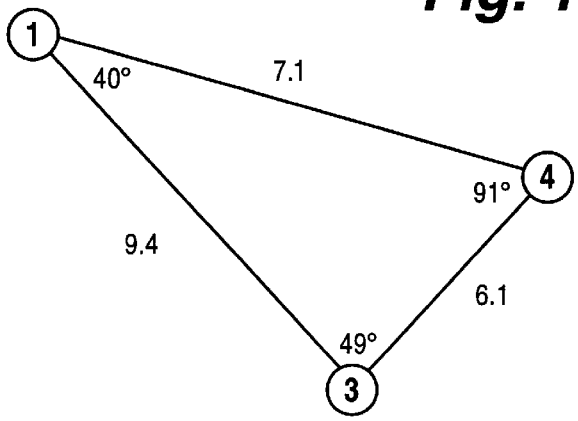
FIG. 18 shows the distance and angle constraints between points 1–3–4 of the pharmacophore of FIG. 4.
Figure 19:
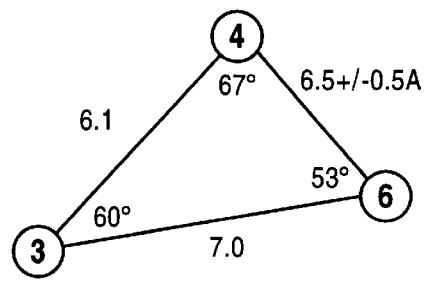
FIG. 19 shows the distance and angle constraints between points 3–4–6 of the pharmacophore of FIG. 4.

FIG. 4 graphically shows the pharmacophore of Der p I. In the figure the Hydrogen bond acceptor is represented by a vector function consisting of two spheres. The smaller sphere (at least 1.6 Angstroms radius up to 2.6 Angstroms) defines the centroid of the hydrogen bond acceptor on the ligand while the large sphere (at least 2.2 Angstroms radius up to 2.6 Angstroms) defines the projected point of the hydrogen bond acceptor from the receptor. These two spheres are at least 3.0 Angstroms apart.

Similarly the Hydrogen bond donor is represented by a two sphere vector function defined in the same way as above for the Hydrogen bond acceptor.

The Hydrophobe features are represented by spheres of at least 1.6 Angstroms radius up to 2.6 Angstroms.

The absolute sphere centroid positions of each feature are defined in three dimensions as follows:

Hydrophobe 1 has Cartesian XYZ co-ordinates of –6.272, 3.372, –1.200

Hydrophobe 2 has co-ordinates of –3.320, –2.305, 0.906

Hydrophobe 3 has co-ordinates of –0.612, –4.088, –1.740

Hydrogen Bond Donor origin co-ordinates of 0.007, 0.926, 4.168

Hydrogen Bond Donor projected point co-ordinates of –0.743, 0.926, 4.168

Hydrogen bond acceptor origin co-ordinates of 5.155, –0.25, –2.528

Hydrogen bond acceptor projected point co-ordinates of 7.413, 0.349, –4.426

The distance constraints are shown in FIGS. 5 and 10 to 19. The angle constraints are shown in FIGS. 6 and 10 to 19.

The tolerances on all distances between the chemical features is +/–0.5 Angstroms and the geometric angles +/–20 Degrees.

REFERENCES

1. Sutton, B. J. & Gould, H. J. *Nature* 366, 421–428 (1993).
2. Flores-Romo, L. et al. *Science* 261, 1038–1041 (1993).
3. Yu, P. et al. *Nature* 369, 753–756 (1994).
4. Stief, A. et al. *J. Immunol.* 152, 3378–3390 (1994).
5. Fujiwara, H. et al. *Proc. Natl. Acad. Sci. USA* 91, 6835–6839 (1994).
6. Chapman, M. D. et al.,*J. Allergy Clin. Immunol.* 72,27–33 (1983).
7. Krillis, S. et al. *J. Allergy Clin. Immunol.* 74,132–141 (1984).
8. Barrett, A. J. et al. *Biochem. J.* 201, 189–198 (1982).
9. Mast, A. E. et al. *Biochemistry* 31, 2720–2728 (1992).
10. Knapp, W. et al. eds. *Leucocyte typing IV,* Oxford University Press. 142–154 (1989).
11. Liu Y. J. et al. *Eur. J. Immunol.* 21, 1107–1114 (1991).
12. Gordon, J. et al. *Immunol. Today* 10, 153–157 (1989).
13. Letellier M. et al. *J. Exp. Med.* 172, 693–700 (1990).
14. Kim, K -M. et al. *Pediatric Res.* 26, 49–53 (1989).
15. Yanagihara, Y. et al. *Clin. Exp. Allergy* 20, 395–401 (1990).
16. Chua, K. Y. et al. *J. Exp. Med.* 167, 175–182 (1988).
17. Finkelman, F. D. & Urban J. F. *Parasitol. Today* 8, 311–314 (1992).
18. Lombardero, M. et. al. *J. Immunol.* 144, 1353–1360 (1990).
19. Ghadieri, A. A. et al. *Immunol. Lett.* 27, 113, (1991).
20. Ghose, A. et al. J. Comp. Chem., 1986, 7, 565–577
21. Smellie, A. et al. J. Comp. Chem., 1995, 16, 171–187
22. Smellie, A. et al. J. Chem. Inf. Comp. Sci., 1995, 35, 285–294
23. Smellie, A. et al. J. Chem. Inf. Comp. Sci., 1995, 35, 295–304
24. Greene, J. et al. J. Chem. Inf. Comp. Sci., 1994, 34, 1297–1308
25. Maeji, N. J. Bray, A. M. Valerio, R. M. and Wang, W., *Peptide Research,* 8(1), 33–38, 1995.
26. Valerio, R. M. Bray, A. M. and Maeji, N. J. *Int. J. Pept. Prot. Res,* 44, 158–165, 1994.

We claim:

1. A compound which has Der p I cysteinyl protease inhibitor activity and is capable of inhibiting proteolytic cleavage of membrane bound CD23 in vivo excluding L-trans-epoxysuccinyl-leucylamido(4-guanidino) butane (E64).

2. A composition capable of adopting a structure essentially equivalent to an inhibitor of the enzyme Der pI, excluding E64, comprising a cysteinyl protease inhibitor compound together with a pharmaceutically acceptable carrier or excipient for use in the treatment of allergic diseases.

3. A cysteinyl protease inhibitor compound which adopts a structure having a pharmacophoric pattern essentially equivalent to the pharmacophoric pattern of a section of an inhibitor of Der p I, excluding E64.

4. A ligand which cross reacts with a cysteinyl protease inhibitor compound which inhibits the enzyme Der p I, excluding E64, which compound which adopts 1 or more copies of a motif which comprises:

i) a hydrogen bond donor;
   ii) three hydrophobes; and
   iii) a hydrogen bond acceptor.

5. A ligand according to claim 4 which comprises a structure essentially equivalent to the pharmacophore defined as follows:

the pharmacophore includes at least 5 chemical features, 3 hydrophobes, a Hydrogen bond acceptor and a Hydrogen Bond Donor; these features being further defined as follows:

(1) the hydrogen bond acceptor feature matches the following atom types or groups of atoms which are surface accessible;

sp or $sp^2$ nitrogens that have a lone pair and a charge less than or equal to zero $sp^3$ oxygens or sulphurs that have a lone pair and charge less than or equal to zero non-basic amines that have a lone pair;

(2) the hydrogen bond donor feature has the same chemical characteristics as the hydrogen bond acceptor except that it also includes basic nitrogen (there is no exclusion of electron-deficient pyridines and imidazoles);

this feature matches the following atom types or groups of atoms;

non-acidic hydroxyls
      thiols
      acetylenic hydrogens
      NH moieties (except tetrazoles and trifluoromethyl sulfonamide hydrogens);

(3) the hydrophobes are defined as a contiguous set of atoms that are not adjacent to a concentration of charge (charged atoms or electronegative atoms), in a conformation such that the atoms have surface accessibility, including phenyl, cycloalkyl, isopropyl, methyl and includes residues which have a partial hydrophobic character such as Lysyl or Glutaminyl amino acid side-chains; and (i) the hydrogen bond acceptor is represented by a vector function consisting of two spheres;

the smaller sphere (at least 1.6 Angstroms radius up to 2.6 Angstroms) defines the centroid of the hydrogen bond acceptor on the ligand while the large sphere (at least 2.2 Angstroms radius up to 2.6 Angstroms) defines the projected point of the hydrogen bond acceptor from the receptor;

these two spheres are at least 3.0 Angstroms apart;

(ii) the hydrogen bond donor is represented by a two sphere vector function as (i) above;

(iii) the hydrophobes are represented by spheres of at least 1.6 Angstroms radius up to 2.6 Angstroms;

and wherein the tolerances on all distances between these features is +/−0.5 Angstroms and the geometric angles +/−20 Degrees and said distances and angles are shown in FIGS. 4, 5 and 10 to 19.

6. A composition for treatment of IgE mediated allergic disease which includes as active ingredient an effective amount of a compound selected from the group consisting of: a cysteinyl protease inhibitor; a substrate for Der p I which reacts with Der p I at a specific site; and a Der p I inhibitor capable of inhibiting the proteolytic enzyme activity of Der p I, the agent optionally including one or more of a pharmaceutically acceptable carrier, adjuvant, excipient.

7. An agent for attenuating or inactivating the allergenicity of Der p I which includes as active ingredient an effective amount of a compound having Der p I inhibitor activity, the agent optionally including one or more of a carrier, adjuvant, excipient.

8. A composition for reducing or destroying the viability of house dust mites which includes as active ingredient an effective amount of a compound having Der p I inhibitor activity, the agent optionally including one or more of a pharmaceutically acceptable carrier, adjuvant, excipient.

9. A process for producing a compound or ligand according to claim 1 which comprises synthesising a cysteinyl protease inhibitor compound or ligand as defined in any of claims 1 to 11 and optionally conjugating said compound or ligand to a carrier.

10. A process according to claim 9 including the further step of isolating and purifying said compound or ligand.

11. A pharmaceutical composition containing as active ingredient at least one compound or ligand according to claim 1 and optionally including an adjuvant or excipient.

12. A pharmaceutical composition according to claim 11 for use in the treatment of an IgE-mediated allergic disease.

13. A pharmaceutical composition according to claim 11 for use in prophylactic prevention of juvenile asthma or eczema.

14. A pharmaceutical composition according to claim 11 for use in the treatment of juvenile asthma or eczema.

* * * * *